United States Patent
Rubin et al.

(10) Patent No.: US 9,750,636 B2
(45) Date of Patent: Sep. 5, 2017

(54) OPHTHALMIC SYSTEM FOR SUSTAINED RELEASE OF DRUG TO EYE

(71) Applicant: ForSight Vision5, Inc., Menlo Park, CA (US)

(72) Inventors: Anne Brody Rubin, Menlo Park, CA (US); Yair Alster, Menlo Park, CA (US); Cary J. Reich, Menlo Park, CA (US)

(73) Assignee: ForSight Vision5, Inc., Menlo Park, CA (US)

( * ) Notice: Subject to any disclaimer, the term of this patent is extended or adjusted under 35 U.S.C. 154(b) by 535 days.

(21) Appl. No.: 14/063,571

(22) Filed: Oct. 25, 2013

(65) Prior Publication Data
US 2014/0121612 A1  May 1, 2014

Related U.S. Application Data

(60) Provisional application No. 61/719,144, filed on Oct. 26, 2012.

(51) Int. Cl.
*A61F 9/00* (2006.01)

(52) U.S. Cl.
CPC .... *A61F 9/0017* (2013.01); *A61F 2250/0067* (2013.01); *Y10T 156/1036* (2015.01)

(58) Field of Classification Search
CPC ........... A61F 9/0017; A61F 2250/0067; Y10T 156/1036
See application file for complete search history.

(56) References Cited

U.S. PATENT DOCUMENTS 3,113,076 A  12/1963  Jacobs
3,312,215 A   4/1967  Silber et al.
(Continued)

FOREIGN PATENT DOCUMENTS

CN  100339058 C  9/2007
EP  1473003 A2  11/2004
(Continued)

OTHER PUBLICATIONS

Kawakita et al.,"Measurement of fornix depth and area: a novel method of determining the severity of fornix shortening", Eye (2009) 23, 1115-1119.
(Continued)

*Primary Examiner* — Tatyana Zalukaeva
*Assistant Examiner* — Benjamin Klein
(74) *Attorney, Agent, or Firm* — Mintz Levin Cohn Ferris Glovsky and Popeo, P.C.

(57) ABSTRACT

Disclosed is an ocular device including a first structure formed of a first material providing a first shape to the ocular device prior to positioning the ocular device on the surface of the eye, a second structure formed of a second, different material having a tubular structure and a lumen through which the first structure extends, and at least one therapeutic agent is dispersed within the second material of the second structure. The first shape of the ocular device conforms to a second, different shape after positioning the ocular device on the surface of the eye. Upon being removed from the eye, the ocular device retains the second shape or changes to a third shape different from both the first shape and the second shape. Related apparatus, systems and method are described.

30 Claims, 15 Drawing Sheets

(56) References Cited

U.S. PATENT DOCUMENTS

| | | |
|---|---|---|
| 3,416,530 A | 12/1968 | Ness |
| 3,545,439 A | 12/1970 | Kalamazoo et al. |
| 3,566,874 A | 3/1971 | Shepherd et al. |
| 3,618,604 A | 11/1971 | Ness |
| 3,626,940 A | 12/1971 | Zaffaroni |
| 3,710,796 A | 1/1973 | Neefe |
| 3,760,805 A | 9/1973 | Higuchi |
| 3,811,444 A | 5/1974 | Heller et al. |
| 3,826,258 A | 7/1974 | Abraham |
| 3,828,777 A | 8/1974 | Ness |
| 3,845,201 A | 10/1974 | Haddad et al. |
| 3,867,519 A | 2/1975 | Michaels |
| 3,903,880 A | 9/1975 | Higuchi et al. |
| 3,916,899 A | 11/1975 | Theeuwes et al. |
| 3,920,805 A | 11/1975 | Roseman |
| 3,926,188 A | 12/1975 | Baker et al. |
| 3,960,150 A | 6/1976 | Hussain et al. |
| 3,961,628 A | 6/1976 | Arnold |
| 3,962,414 A | 6/1976 | Michaels |
| 3,963,025 A | 6/1976 | Whitaker et al. |
| 3,991,760 A | 11/1976 | Drobish et al. |
| 3,993,073 A | 11/1976 | Zaffaroni |
| 3,995,633 A | 12/1976 | Gougeon |
| 3,995,634 A | 12/1976 | Drobish |
| 3,995,635 A | 12/1976 | Higuchi et al. |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,335 A | 3/1977 | Arnold |
| 4,016,251 A | 4/1977 | Higuchi et al. |
| 4,052,505 A | 10/1977 | Higuchi et al. |
| 4,057,619 A | 11/1977 | Higuchi et al. |
| 4,067,961 A | 1/1978 | Laughlin |
| 4,093,709 A | 6/1978 | Choi et al. |
| 4,131,648 A | 12/1978 | Choi et al. |
| 4,155,991 A | 5/1979 | Schopflin et al. |
| 4,157,864 A | 6/1979 | Koller et al. |
| 4,160,452 A | 7/1979 | Theeuwes |
| 4,164,560 A | 8/1979 | Folkman et al. |
| 4,177,256 A | 12/1979 | Michaels et al. |
| 4,179,497 A | 12/1979 | Cohen et al. |
| 4,190,642 A | 2/1980 | Gale et al. |
| 4,201,210 A | 5/1980 | Hughes et al. |
| 4,215,691 A | 8/1980 | Wong |
| 4,249,531 A | 2/1981 | Heller et al. |
| 4,281,654 A | 8/1981 | Shell et al. |
| 4,285,987 A | 8/1981 | Ayer et al. |
| 4,292,965 A | 10/1981 | Nash et al. |
| 4,303,637 A | 12/1981 | Shell et al. |
| 4,304,765 A | 12/1981 | Shell et al. |
| 4,322,323 A | 3/1982 | Capozza |
| 4,343,787 A | 8/1982 | Katz |
| 4,432,964 A | 2/1984 | Shell et al. |
| 4,439,198 A | 3/1984 | Brightman, II et al. |
| 4,469,671 A | 9/1984 | Zimmerman et al. |
| 4,484,922 A | 11/1984 | Rosenwald |
| 4,524,776 A | 6/1985 | Withers et al. |
| 4,540,417 A | 9/1985 | Poler |
| 4,652,099 A | 3/1987 | Lichtman |
| 4,678,466 A | 7/1987 | Rosenwald |
| 4,822,616 A | 4/1989 | Zimmermann et al. |
| 4,888,074 A | 12/1989 | Pocknell |
| 4,961,931 A | 10/1990 | Wong |
| 4,973,304 A | 11/1990 | Graham et al. |
| 5,071,657 A | 12/1991 | Oloff et al. |
| 5,098,443 A | 3/1992 | Parel et al. |
| 5,137,728 A | 8/1992 | Bawa |
| 5,147,647 A | 9/1992 | Darougar |
| 5,178,635 A | 1/1993 | Gwon et al. |
| 5,205,611 A | 4/1993 | Stephens |
| 5,248,700 A | 9/1993 | Lance |
| 5,300,114 A | 4/1994 | Gwon et al. |
| 5,314,419 A | 5/1994 | Pelling |
| 5,322,691 A | 6/1994 | Darougar et al. |
| 5,370,607 A | 12/1994 | Memmen |
| 5,378,475 A | 1/1995 | Smith et al. |
| 5,395,618 A | 3/1995 | Darougar et al. |
| 5,443,505 A | 8/1995 | Wong et al. |
| 5,472,436 A | 12/1995 | Fremstad |
| 5,474,780 A | 12/1995 | Chang |
| 5,476,511 A | 12/1995 | Gwon et al. |
| 5,496,811 A | 3/1996 | Aviv et al. |
| 5,605,696 A | 2/1997 | Eury et al. |
| 5,618,274 A | 4/1997 | Rosenthal |
| 5,694,947 A | 12/1997 | Lehtinen et al. |
| 5,773,019 A | 6/1998 | Ashton et al. |
| 5,773,021 A | 6/1998 | Gurtler et al. |
| 5,788,977 A | 8/1998 | Aguadisch et al. |
| 5,824,086 A | 10/1998 | Silvestrini |
| 5,851,547 A | 12/1998 | Fujioka et al. |
| 5,855,906 A | 1/1999 | McClay |
| 5,902,598 A | 5/1999 | Chen et al. |
| 5,972,372 A | 10/1999 | Saleh et al. |
| 5,989,579 A | 11/1999 | Darougar et al. |
| 6,001,386 A | 12/1999 | Ashton et al. |
| 6,015,213 A * | 1/2000 | Nakada .................. G02C 7/04 351/159.48 |
| 6,096,076 A | 8/2000 | Silvestrini |
| 6,109,537 A | 8/2000 | Heath |
| 6,120,460 A | 9/2000 | Abreu |
| 6,146,366 A | 11/2000 | Schachar |
| 6,149,685 A | 11/2000 | Sigoloff |
| 6,217,896 B1 | 4/2001 | Benjamin |
| 6,264,971 B1 | 7/2001 | Darougar et al. |
| 6,361,780 B1 | 3/2002 | Ley et al. |
| 6,375,642 B1 | 4/2002 | Grieshaber et al. |
| 6,375,972 B1 | 4/2002 | Guo et al. |
| 6,394,094 B1 | 5/2002 | McKenna et al. |
| 6,485,735 B1 | 11/2002 | Steen et al. |
| 6,547,714 B1 | 4/2003 | Dailey |
| 6,634,576 B2 | 10/2003 | Verhoff et al. |
| 6,669,950 B2 | 12/2003 | Yaacobi |
| 6,719,750 B2 | 4/2004 | Varner et al. |
| 6,746,686 B2 | 6/2004 | Hughes et al. |
| 6,841,574 B2 | 1/2005 | Mo et al. |
| 6,939,569 B1 | 9/2005 | Green et al. |
| 6,964,781 B2 | 11/2005 | Brubaker |
| 6,966,927 B1 | 11/2005 | Silverstrini |
| 6,986,900 B2 | 1/2006 | Yaacobi |
| 6,991,808 B2 | 1/2006 | Brubaker et al. |
| 7,094,226 B2 | 8/2006 | Yaacobi |
| 7,195,774 B2 | 3/2007 | Carvalho et al. |
| 7,488,343 B2 | 2/2009 | O'Brien et al. |
| 7,544,371 B2 | 6/2009 | Kunzler et al. |
| 7,785,578 B2 | 8/2010 | Miller et al. |
| 7,799,336 B2 | 9/2010 | Hughes |
| 7,833,545 B2 | 11/2010 | Ron et al. |
| 7,862,552 B2 | 1/2011 | McIntyre et al. |
| 7,910,126 B2 | 3/2011 | Ahmed et al. |
| 7,985,208 B2 | 7/2011 | Christensen |
| 7,998,497 B2 | 8/2011 | de Juan, Jr. et al. |
| 8,021,680 B2 | 9/2011 | Anderson et al. |
| 8,715,712 B2 | 5/2014 | de Juan, Jr. et al. |
| 2002/0026176 A1 | 2/2002 | Varner et al. |
| 2002/0047058 A1 | 4/2002 | Verhoff et al. |
| 2002/0115985 A1 | 8/2002 | Larson et al. |
| 2003/0088307 A1 | 5/2003 | Shulze et al. |
| 2003/0176854 A1 | 9/2003 | Rodstrom |
| 2004/0042073 A1 | 3/2004 | Pynson |
| 2004/0115234 A1 | 6/2004 | Gewirtz |
| 2004/0121014 A1 | 6/2004 | Guo et al. |
| 2004/0133155 A1 | 7/2004 | Varner et al. |
| 2004/0170685 A1 | 9/2004 | Carpenter et al. |
| 2004/0220660 A1 | 11/2004 | Shanley et al. |
| 2004/0241243 A1 | 12/2004 | Lin et al. |
| 2004/0249364 A1 | 12/2004 | Kaploun |
| 2004/0265355 A1 | 12/2004 | Shalaby |
| 2005/0019371 A1 | 1/2005 | Anderson et al. |
| 2005/0042292 A1 | 2/2005 | Muldoon et al. |
| 2005/0048099 A1 | 3/2005 | Shiah et al. |
| 2005/0053639 A1 | 3/2005 | Shalaby |
| 2005/0060021 A1 | 3/2005 | O'Brien et al. |
| 2005/0125059 A1 | 6/2005 | Pinchuk et al. |
| 2005/0163844 A1 | 7/2005 | Ashton |

(56) References Cited

U.S. PATENT DOCUMENTS

| | | |
|---|---|---|
| 2005/0196424 A1 | 9/2005 | Chappa |
| 2005/0197651 A1 | 9/2005 | Chen et al. |
| 2005/0228473 A1 | 10/2005 | Brown |
| 2005/0228482 A1 | 10/2005 | Herzog et al. |
| 2005/0244461 A1 | 11/2005 | Nivaggioli et al. |
| 2005/0244464 A1 | 11/2005 | Hughes |
| 2005/0276841 A1 | 12/2005 | Davis et al. |
| 2006/0024350 A1 | 2/2006 | Varner et al. |
| 2006/0034891 A1 | 2/2006 | Lawin et al. |
| 2006/0140867 A1 | 6/2006 | Helfer et al. |
| 2006/0185678 A1 | 8/2006 | Bronnenkant et al. |
| 2006/0212115 A1 | 9/2006 | Maldonado Bas |
| 2006/0216328 A1 | 9/2006 | Kis et al. |
| 2006/0235513 A1 | 10/2006 | Price |
| 2006/0246112 A1 | 11/2006 | Snyder et al. |
| 2006/0264912 A1 | 11/2006 | McIntyre et al. |
| 2006/0292222 A1 | 12/2006 | Jonasse |
| 2007/0112318 A1 | 5/2007 | Leahy et al. |
| 2007/0134305 A1 | 6/2007 | Zilberman |
| 2007/0196433 A1 | 8/2007 | Ron et al. |
| 2007/0202150 A1 | 8/2007 | Dave |
| 2007/0212387 A1 | 9/2007 | Patravale et al. |
| 2007/0243230 A1 | 10/2007 | de Juan et al. |
| 2007/0269487 A1 | 11/2007 | de Juan et al. |
| 2008/0090911 A1 | 4/2008 | Frank et al. |
| 2008/0097591 A1 | 4/2008 | Savage et al. |
| 2008/0103584 A1 | 5/2008 | Su et al. |
| 2008/0145406 A1 | 6/2008 | Asgharian et al. |
| 2008/0181930 A1 | 7/2008 | Rodstrom et al. |
| 2008/0243095 A1 | 10/2008 | Kaiser et al. |
| 2009/0005864 A1 | 1/2009 | Eggleston |
| 2009/0012836 A1 | 1/2009 | Weissbach et al. |
| 2009/0081278 A1 | 3/2009 | De Graaff et al. |
| 2009/0082863 A1 | 3/2009 | Schieber et al. |
| 2009/0092654 A1 | 4/2009 | de Juan, Jr. et al. |
| 2009/0104243 A1 | 4/2009 | Utkhede et al. |
| 2009/0104248 A1 | 4/2009 | Rapacki et al. |
| 2009/0143752 A1 | 6/2009 | Higuchi et al. |
| 2009/0148485 A1 | 6/2009 | Whitehead |
| 2009/0155326 A1 | 6/2009 | Mack et al. |
| 2009/0155338 A1 | 6/2009 | Conway et al. |
| 2009/0162417 A1 | 6/2009 | Eells |
| 2009/0196903 A1 | 8/2009 | Kliman |
| 2009/0220573 A1 | 9/2009 | Kaufman |
| 2009/0234005 A1 | 9/2009 | Ishida et al. |
| 2009/0252807 A1 | 10/2009 | Jenkins et al. |
| 2009/0280158 A1 | 11/2009 | Butuner |
| 2009/0287300 A1 | 11/2009 | Dave et al. |
| 2009/0291120 A1 | 11/2009 | Tuominen et al. |
| 2009/0318549 A1 | 12/2009 | Butuner |
| 2010/0040671 A1 | 2/2010 | Ahmed et al. |
| 2010/0055139 A1 | 3/2010 | Lee |
| 2010/0069857 A1 | 3/2010 | Christensen |
| 2010/0074942 A1 | 3/2010 | Ratner et al. |
| 2010/0114309 A1 | 5/2010 | de Juan, Jr. et al. |
| 2010/0124565 A1 | 5/2010 | Spada et al. |
| 2010/0166841 A1 | 7/2010 | Roth et al. |
| 2010/0178316 A1 | 7/2010 | Chauhan et al. |
| 2010/0209477 A1 | 8/2010 | Butuner et al. |
| 2010/0209478 A1 | 8/2010 | Sawhney et al. |
| 2010/0226962 A1 | 9/2010 | Rodstrom et al. |
| 2010/0233241 A1 | 9/2010 | Leahy et al. |
| 2010/0266664 A1 | 10/2010 | Asgharian et al. |
| 2010/0278898 A1 | 11/2010 | Hughes et al. |
| 2010/0331796 A1 | 12/2010 | Leahy et al. |
| 2011/0009958 A1 | 1/2011 | Wardle et al. |
| 2011/0105986 A1 | 5/2011 | Bronstein et al. |
| 2011/0184358 A1 | 7/2011 | Weiner et al. |
| 2011/0195123 A1 | 8/2011 | Shemi |
| 2011/0268783 A1 | 11/2011 | Shalaby et al. |
| 2011/0280909 A1 | 11/2011 | Moazed |
| 2011/0282328 A1 | 11/2011 | Ambati et al. |
| 2012/0022473 A1 | 1/2012 | Shikamura et al. |
| 2012/0089072 A1 | 4/2012 | Cunningham, Jr. |
| 2012/0109054 A1 | 5/2012 | Thompson et al. |
| 2012/0136322 A1 | 5/2012 | Alster et al. |
| 2012/0177716 A1 | 7/2012 | Ho et al. |
| 2012/0187594 A1 | 7/2012 | Utkhede et al. |
| 2012/0215184 A1 | 8/2012 | Lim |
| 2012/0245505 A1 | 9/2012 | Robinson et al. |
| 2012/0269893 A1 | 10/2012 | Lee |
| 2013/0062809 A1 | 3/2013 | Ellis et al. |
| 2013/0090612 A1 | 4/2013 | de Juan, Jr. et al. |
| 2013/0142858 A1 | 6/2013 | Kopczynski et al. |
| 2013/0144128 A1 | 6/2013 | de Juan, Jr. et al. |
| 2013/0156752 A1 | 6/2013 | Jarrett et al. |
| 2013/0177615 A1 | 7/2013 | Lee |
| 2013/0209538 A1 | 8/2013 | Venkatraman et al. |
| 2013/0261569 A1 | 10/2013 | Weiner et al. |
| 2015/0133878 A1 | 5/2015 | de Juan, Jr. et al. |

FOREIGN PATENT DOCUMENTS

| | | | |
|---|---|---|---|
| GB | 1372944 | | 11/1974 |
| GB | 1529143 A | | 10/1978 |
| JP | S48-036993 | | 5/1973 |
| JP | S5560452 | | 5/1980 |
| JP | 2007167358 | | 7/2007 |
| RU | 2357709 C1 | | 6/2009 |
| WO | WO-92/14450 A1 | | 9/1992 |
| WO | WO-97/43984 A1 | | 11/1997 |
| WO | WO-02076426 A2 | | 10/2002 |
| WO | WO-2005/020907 A3 | | 7/2005 |
| WO | WO-2007083293 A1 | | 7/2007 |
| WO | WO-2009035562 A2 | | 3/2009 |
| WO | WO-2010141729 | | 12/2010 |
| WO | WO 2010141729 A1 * | 12/2010 | ........... A61F 9/0017 |

OTHER PUBLICATIONS

Zeus Technical Newsletter. "Strength and Stiffness of Plastics". (Obtained from http://www.zeusinc.com/UserFiles/zeusinc/Documents/technical_newsletters/Zeus_StrengthStiffnessPlastics.pdf on Oct. 18, 2013).

* cited by examiner

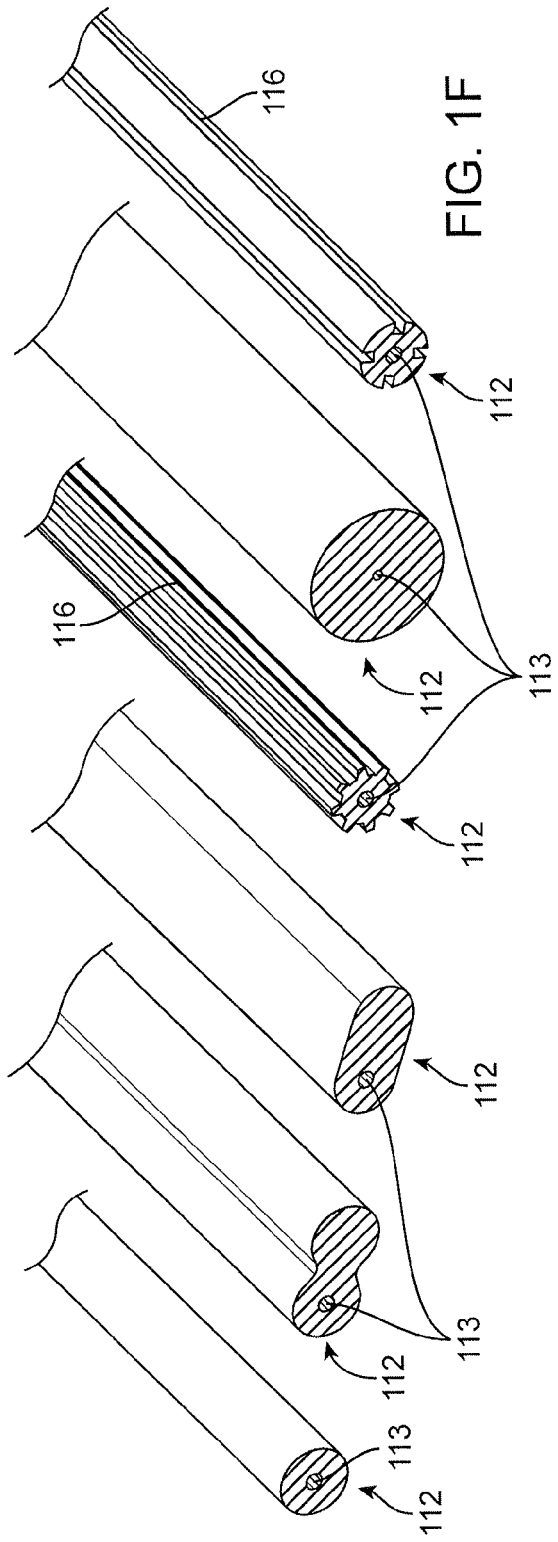
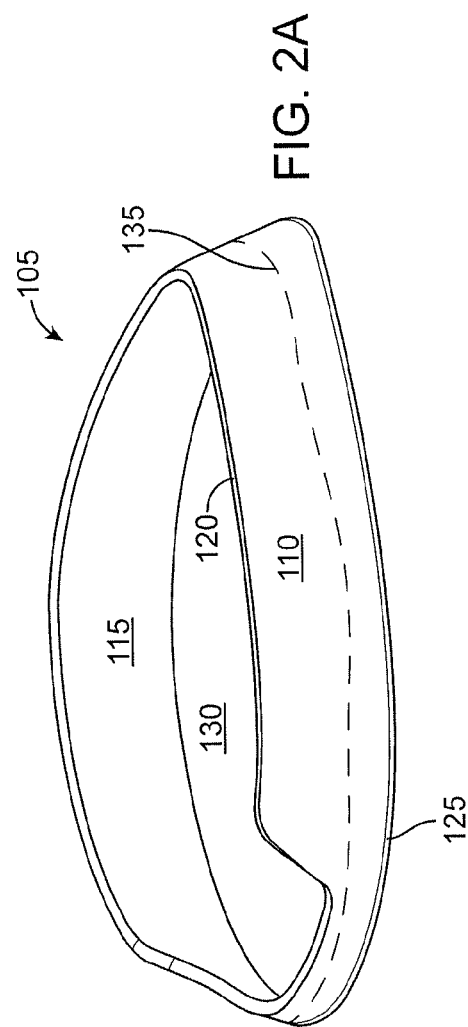
FIG. 1F
FIG. 2A

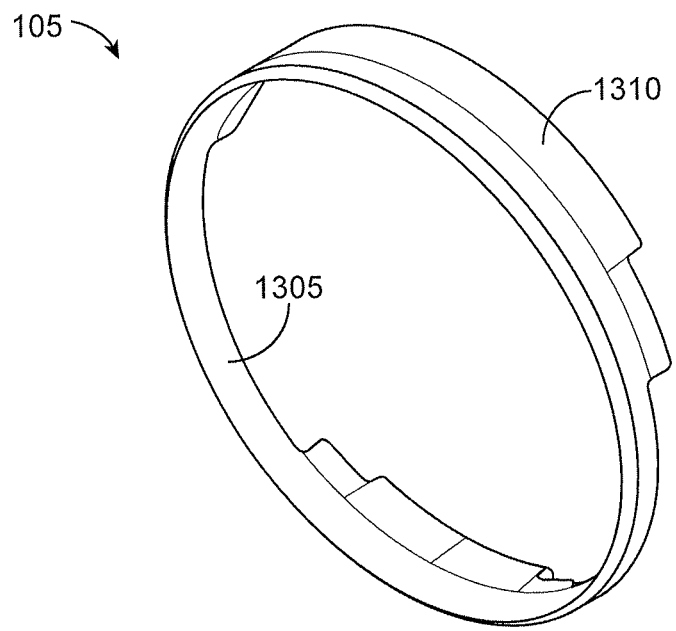
FIG. 9
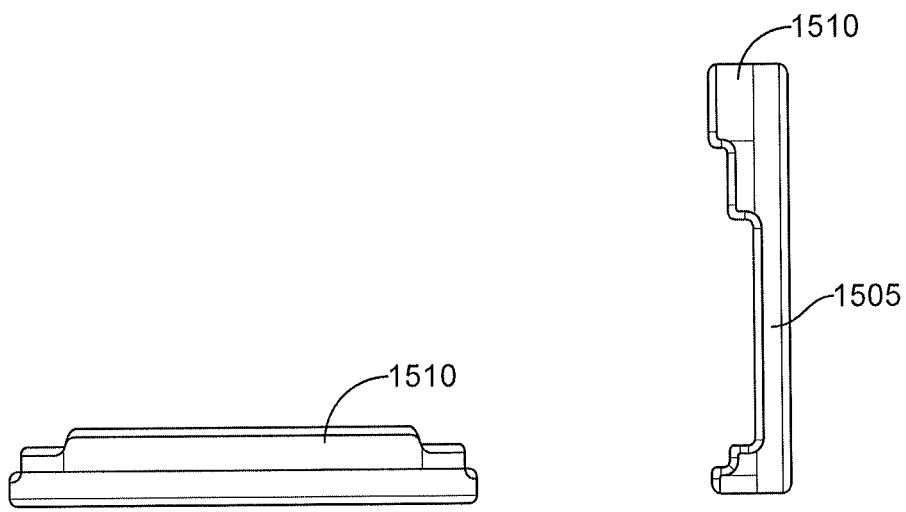
FIG. 10
FIG. 11

OPHTHALMIC SYSTEM FOR SUSTAINED RELEASE OF DRUG TO EYE

REFERENCE TO PRIORITY DOCUMENT

This application claims priority of U.S. Provisional Patent Application Ser. No. 61/719,144, entitled "Ophthalmic System for Sustained Release of Drug to Eye," filed Oct. 26, 2012. Priority of the filing date is hereby claimed and the disclosure of the provisional patent application is hereby incorporated by reference in its entirety.

RELATED APPLICATIONS

This application is related to (1) U.S. Patent Publication No. 2012/0136322, entitled ANTERIOR SEGMENT DRUG DELIVERY, filed Jun. 1, 2011; and (2) U.S. Patent Publication No. 2013/0144128 entitled OCULAR INSERT APPARATUS AND METHODS, filed Sep. 14, 2012, both of which are incorporated herein by reference in their entirety.

BACKGROUND

Described herein are structures, systems, and methods for placement of an ocular device on an eye that may be used to treat the eye. Provided are various implementations of ocular devices used for drug delivery, along with methods for using ocular devices positioned on or near the anterior surface of the eye. The devices may be worn along an anterior surface of the eye outside the optical zone, and can deliver therapeutically efficacious amounts of one or more therapeutic agents.

A variety of ophthalmic and non-ophthalmic conditions necessitate administration of various drugs to the eye. Eye drops and gels can be effective drug delivery vehicles, but can also have significant disadvantages. Specifically, eye drops mix with fluid in the tear film, but may have a residence time of only 2-5 minutes in the tear film. As little as 5% of the drug may be absorbed locally; some or all of the rest being carried from the lacrimal sac into the lacrimal duct, which can have potentially undesirable effects. Consequently, most of the drug may be wasted with less than ideal amounts delivered to the targeted tissue. Also, the presence of the drug in the bloodstream may have potentially harmful side effects. Gels may adhere more effectively to the eye, but can also blur the patient's vision. Both eye drops and gels may need to be reapplied frequently for some therapies, and patients may not administer the eye drops or gels as frequently as directed in at least some instances, such that the amount of drug delivered can be less than ideal. For example, in at least some instances a substantial number of patients may not refill their prescription after one year, and the substantial number of patients can be up to fifty percent in some instances. Alternatives to eye drops and gels include treatments in which insert structures containing or impregnated with drugs have been placed under an eyelid, in a punctum, or on the cornea with drug-impregnated contact lenses, and the like.

SUMMARY

A need remains for improved drug delivery to the eye having less frequent user application and providing improved regularity of the amount of drug delivered to the eye.

In one aspect, there is disclosed an ocular device configured to be positioned on a surface of the eye at least partially underneath at least one of the upper and lower eyelids and outside a cornea of the eye for delivering at least one therapeutic agent to an eye for an extended period of time. The device includes a first structure formed of a first material providing a first shape to the ocular device prior to positioning the ocular device on the surface of the eye. The device includes a second structure formed of a second material having a tubular structure and a lumen through which the first structure extends. The second material is different from the first material. The device includes at least one therapeutic agent dispersed within the second material of the second structure. The first shape of the ocular device conforms to a second, different shape after positioning the ocular device on the surface of the eye. Upon being removed from the eye, the ocular device retains the second shape or changes to a third shape. The third shape is different from both the first shape and the second shape.

The tubular structure can have a cross-sectional shape that is circular, lentoid, figure-eight, horseshoe, oval, oblong, rounded rectangle, star or gear-shaped. The first structure can be thermally fused into a ring shape after being threaded through the lumen of the second structure. The second structure can be formed of a second material molded into two or more tubular structures. Each of the two or more tubular structures can have a lumen through which the first structure extends. A first of the two or more tubular structures can be formulated to release the at least one therapeutic agent and a second of the two or more tubular structures can be formulated to release the at least one therapeutic agent or a second, different therapeutic agent. The first structure can determine the first shape, the second shape and the third shape. The second shape can be a shape of at least a portion of the conjunctiva of the eye, at least a portion of the bony orbit of the eye, or at least a portion of bony orbit of the eye.

The ocular device can resist deflection away from the second shape upon being removed from the eye. The first shape can be an annular shape positioned substantially within a first plane and the second and third shapes are positioned at least partially outside of the first plane. The second shape can correspond to a surface of a saddle. The second shape can have an outer contour that corresponds to an outer contour of a saddle. The ocular device can change from the first shape to the second shape over a period of about 20 minutes to about 24 hours. The first material can include a material configured to repeatedly become plastic upon exposure to heat, liquid, or pressure. The first material can include a thermoplastic material. The first material can include polypropylene. The second material can include a silicone material. In some implementations, only the second material includes the at least one therapeutic agent.

The at least one therapeutic agent can include bimatoprost, travoprost, latanoprost, tafluprost, NSAID, steroid, antihistamine, carbonic anhydrase inhibitor (CAI), dorzolamide, cyclosporine, antibiotic, doxycycline, tetracycline, azithromycin, fatty acid, long chain fatty acid, fatty alcohol, cetyl alcohol, stearyl alcohol, non-penetrating steroid, free acid of steroid, lipid, ketorolac, silicone oil, olopatadine, prostaglandin, prostaglandin analog, prostamide, small-molecule integrin antagonist, lifitegrast, loteprednol, and fluorometholone or a combination thereof. The at least one therapeutic agent can include a prostaglandin analogue. The prostaglandin analogue can include at least one of bimatoprost, latanoprost, travoprost, and tafluprost. The at least one therapeutic agent can be for lowering the intraocular pressure of the eye. The at least one therapeutic agent can be for treating dry eye. The at least one therapeutic agent can include at least one of cyclosporine, steroid, loteprednol, fluoromethalone, non-penetrating steroid, free acid of steroid, non-steroidal anti-inflammatory, ketorolac, small-molecule integrin antagonist, lifitegrast, doxycycline, azithromycin, lipid, fatty alcohol, cetyl alcohol, stearyl alcohol, fatty acid, long chain fatty acid, oil, or silicone oil. The at least one therapeutic agent can include a steroid. The steroid can include at least one of loteprednol or fluoromethalone.

In an interrelated aspect, disclosed is an ocular device configured to be positioned on a surface of the eye at least partially underneath at least one of the upper and lower eyelids and outside a cornea of the eye for delivering at least one therapeutic agent to an eye for an extended period of time. The device includes a first structure formed of a first material providing a first shape to the ocular device prior to positioning the ocular device on the surface of the eye. The device includes a second structure formed of a second material having a tubular structure with a lumen through which the first structure extends. The second material is different from the first material. The device includes at least one therapeutic agent dispersed within the first material of the first structure. The first shape of the ocular device conforms to a second, different shape after positioning the ocular device on the surface of the eye. Upon being removed from the eye, the ocular device retains the second shape or changes to a third shape. The third shape is different from both the first shape and the second shape.

In an interrelated aspect, disclosed is a method of manufacturing an ocular device configured to be positioned on a surface of the eye at least partially underneath at least one of the upper and lower eyelids and outside a cornea of the eye for delivering at least one therapeutic agent to an eye for an extended period of time. The method includes forming a support structure from a length of a first material having a first end region and a second end region into a first shape. The first shape of the support structure provides an overall shape to the ocular device prior to positioning the ocular device on the surface of the eye. The method includes dispersing at least one therapeutic agent into a second material to create a drug matrix. The second material is different from the first material. The method includes molding the drug matrix into a tubular structure having lumen. The method includes threading the tubular structure over the length the support structure such that the support structure extends through the lumen of the tubular structure. The first shape conforms to a second, different shape after positioning the ocular device onto the surface of the eye. Upon being removed from the eye, the ocular device retains the second shape or changes to a third shape. The third shape is different from both the first shape and the second shape.

The method can further include fusing the first end region of the length to the second end region of the length after the support structure is threaded through the lumen of the tubular structure. Fusing can include thermally welding the first and second end regions together. The method can further include thermoforming the length into the first shape by wrapping the length over a mandrel having a diameter. The diameter can be at least about 24 mm, at least about 26 mm, or at least about 29 mm. The support structure can determine the first shape, the second shape and the third shape of the ocular device. The first shape can be an annular shape positioned substantially within a first plane and the second and third shapes are positioned at least partially outside of the first plane. The ocular device can change from the first shape to the second shape over a period of about 20 minutes to about 24 hours. The first material can include a material configured to repeatedly become plastic upon exposure to heat, liquid, or pressure. The first material can include a thermoplastic material. The first material can include polypropylene. The second material can include a silicone material.

The at least one therapeutic agent can include bimatoprost, travoprost, latanoprost, tafluprost, NSAID, steroid, antihistamine, carbonic anhydrase inhibitor (CAI), dorzolamide, cyclosporine, antibiotic, doxycycline, tetracycline, azithromycin, fatty acid, long chain fatty acid, fatty alcohol, cetyl alcohol, stearyl alcohol, non-penetrating steroid, free acid of steroid, lipid, ketorolac, silicone oil, olopatadine, prostaglandin, prostaglandin analog, prostamide, small-molecule integrin antagonist, lifitegrast, loteprednol, and fluorometalone or a combination thereof. The tubular structure can have a cross-sectional shape including circular, lentoid, figure-eight, horseshoe, oval, oblong, rounded rectangle, star or gear-shaped. The tubular structure can have a cross-sectional diameter of approximately 1 mm.

The method can further include releasing the at least one therapeutic agent from the drug matrix into the eye. The method can further include dispersing at least a second therapeutic agent into a second amount of the second material to create a second amount of drug matrix and molding the second amount of drug matrix into at least a second tubular structure having a second lumen. The method can further include threading the at least a second tubular structure over the length of the support structure such that the support structure extends through the second lumen of the at least a second tubular structure. The method can further include releasing the at least a second therapeutic agent from the second amount of drug matrix. The at least a second therapeutic agent can be the same as the at least one therapeutic agent. The at least a second therapeutic agent can be different from the at least one therapeutic agent. The drug matrix can release the at least one therapeutic agent into the eye at a first elution rate and the second amount of drug matrix can release the at least a second therapeutic agent into the eye at a second elution rate. The first elution rate and the second elution rate can be the same or different.

Other features and advantages should be apparent from the following description of various implementations, which illustrate, by way of example, the principles of the invention.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements can be modified for the purpose of illustrative clarity.

FIG. 1F shows examples of cross-sectional shapes of the ocular devices described herein;

FIG. 2A shows a perspective view of another implementation of an ocular device;

FIG. 9 shows a perspective view of another implementation of an ocular device;

FIG. 10 shows a side view of the ocular device of FIG. 9;

FIG. 11 shows a side view of the ocular device of FIG. 9;

Figure 1A:
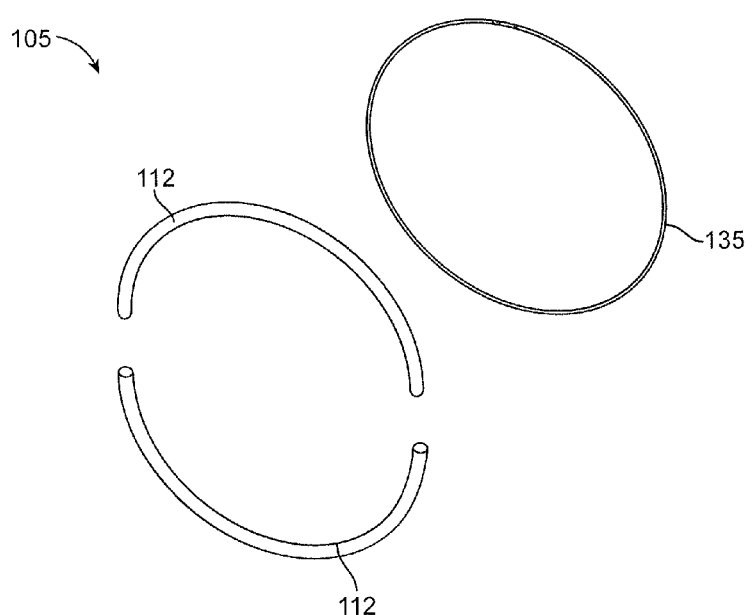
FIG. 1A shows an exploded view of an implementation of an ocular device.

It should be appreciated that the drawings herein are for example only and are not meant to be to scale.

DETAILED DESCRIPTION

Disclosed herein are various implementations of ocular devices that are configured to be positioned on an outer, or anterior, surface of an eye for delivering a therapeutic substance to the eye. The ocular devices described herein are coupled to a therapeutic substance. In this regard, the ocular devices are made of, coated with, contains, or are otherwise coupled to a therapeutic substance, as described in detail below. The ocular devices are sized and shaped such that the device is configured to be positioned on an outer surface of the eye with at least a portion of the ocular device positioned under one or both eyelids in a manner that does not contact or interfere with the cornea.

The ocular devices described herein are sized and shaped such that the ocular device maintains itself in a generally fixed position on the eye so as to avoid undesired movement once positioned on the eye. The ocular devices can be configured in many ways and can be configured to fix in place and/or slightly move when placed on the eye so as to provide improved comfort for the patient. The fixation and/or relative movement of the ocular devices can be relative to the globe of the eye or relative to anatomical structure(s) adjacent the eye, such as the conjunctival fornices.

As will be described in more detail below, the ocular devices described herein can be in situ formable. In this regard, an implementation of the ocular device has a first shape prior to being positioned in the eye. That is, the ocular device in a stand-alone state has a first shape. The ocular device can then be positioned on the eye such that the ocular device takes on a second shape that is different from the first shape. With respect to the second shape, the ocular device can mold to the second shape and/or plastically take on the second shape. The ocular device can also be activated to take on the second shape, for example using shape memory capabilities of the material from which the ocular device can at least partially be manufactured. Upon removal from the eye, the ocular device can retain the second shape. That is, the ocular device can maintain the second shape even after being removed from the eye. Or, upon removal from the eye, the ocular device can change to a third shape that is different from the first shape and/or the second shape. The change in shape can occur in two or three dimensions and can occur over any of an x-, y-, or z-axis relative to the ocular device.

With respect to the transition to the second shape, the ocular device is configured to transition to a shape that conforms to or complements a shape of anatomy of the eye itself and/or anatomy around the eye. For example, the ocular device can conform to a second shape that corresponds to the contour and dimensions of the anterior surface of the eye. In another implementation, the ocular device can conform to a second shape that corresponds to the shape of anatomy around or adjacent the eye. Such anatomy can include, for example, the eyelid(s), conjunctival folds, medial canthus, lateral canthus, superior oblique muscle, trochlea, lacrimal gland, etc.

The transition from the first shape (outside of the eye) to the second shape (positioned on the eye) can occur over a period of time. For example, the transition can initially start within minutes, days, or months from the time the ocular device is initially placed on the eye. The transition to the second shape can be completed over a period of less than a minute, one or more minutes, a period of days, or a period of months from the time the ocular device is initially placed on the eye and can be selected to conform to one or more requirements.

The ocular device to be positioned on the eye can be selected from a plurality of such ocular devices, wherein the selection is at least partially based on the overall size of the ocular device relative to the overall size of the eye on which the ocular device is to be placed, such as the diameter of the eye. In an implementation, the ocular device, when in the first shape, has a maximum diameter that is greater than the maximum diameter of the eye on which the ocular device is to be placed.

Because the ocular device can conform or complement the shape of anatomy of the eye after implantation, no specific knowledge of the patient's eye shape is necessary. The ocular devices described herein can become tailored to fit the patient's eye anatomy in situ after the device is placed on the patient's eye. The ocular devices described herein can readily conform without applying a substantial force against the eye anatomy, such as to return to the first shape prior to implantation, which can impair patient comfort and result in a patient feel the device in position. The ocular devices described herein, however, are not so limp that they cannot be readily handled by a physician during positioning and removal.

Ocular Devices

Several implementations of the ocular device are now described.

Figure 1B:
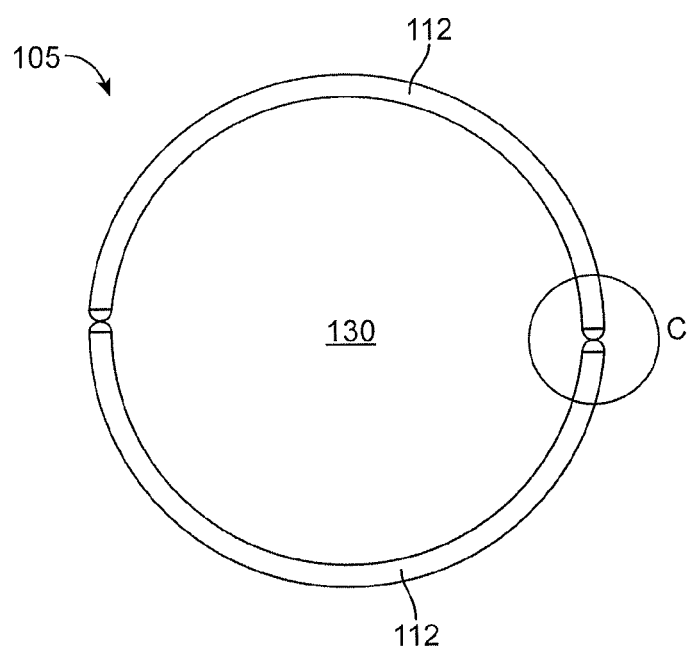
FIG. 1B shows a perspective, assembled view of the ocular device of FIG. 1A.
Figure 1C:
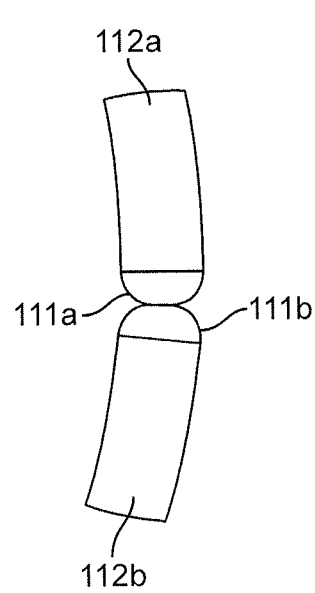
FIG. 1C shows a detailed view of the ocular device of FIG. 1B taken along circle C.
Figure 1D:
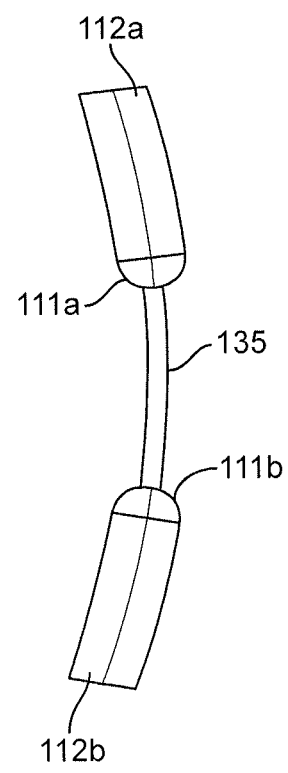
FIG. 1D shows a detailed view of another implementation of an ocular device.
Figure 1E:
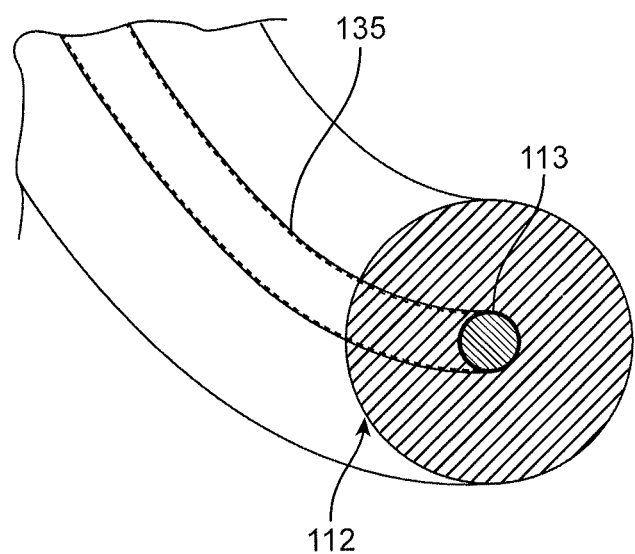
FIG. 1E shows a cross-sectional view of the ocular device of FIG. 1B.

FIG. 1A shows an exploded view, FIG. 1B shows an assembled view and FIG. 1E shows a cross-sectional view of one implementation of an ocular device 105. The ocular device 105 can have an annular configuration, such as an oval, circle or toroid, with an opening 130 that can be sized and shaped to fit outside the corneal diameter when positioned on the anterior surface of the eye. The ocular device 105 can include one or more body structures 112 configured to surround, cover or be coupled to at least a portion of a support structure 135. In some implementations, the entire length of the support structure 135 is surrounded or covered by the one or more body structures 112. In some implementations, the support structure 135 is an inner support structure that extends through an inner channel or lumen 113 of the one or more body structures 112 (see FIG. 1E and FIG. 1F). The lumen 113 can have an inner diameter configured to receive or contain the support structure 135 such that the support structure 135 can be threaded through the lumen 113. The lumen 113 extending through the one or more body structures 112 can be located centrally (such as shown in FIG. 1E) or off-center (such as in the rounded rectangle and figure eight versions shown in FIG. 1F). Further, the one or more body structures 112 can include one or more grooves 116 on an outer surface such that the support structure 135 can be coupled to or extend through the grooves 116 of the one or more body structures 112 rather than or in addition to being threaded through the inner lumen 113. Whether the support structure 135 is located within an inner lumen 113 or an outer groove 116 of the one or more body structures 112, at least a portion of the one or more body structures 112 can be configured to contact the eye's anterior outer surface when the ocular device 105 is positioned on the eye.

The support structure 135 can have any of a variety of materials, shapes and thicknesses. The support structure 135 can be a non-erodible material that can determine the overall shape of the device 105. The support structure 135 can form a thin, elongated structure that can be wire-like in stiffness and formable into an overall shape of the device, such as a ring shape or other form. The support structure 135 can be formed of any of a variety of materials including, but not limited to thin metal wire or wires, a monofilament or series of monofilaments, a hard plastic such as nylon, PMMA, polycarbonate, polyethylene terephthalate, and/or another polymer, polypropylene or other synthetic suture material capable of providing the structural support to the device 105. In an implementation, the support structure 135 is a wire. In another implementation, the support structure 135 is a polypropylene monofilament or series of filaments fused together at the terminal ends to form a ring structure. The support structure 135 can be heat-set into a ring shape or other shape. The support structure 135 can be capable of activating after the ocular device 105 is inserted onto the eye so as to cause the ocular device 105 to conform in situ. For example, the material of the support structure can be thermally activated, for example through heat imparted to the insert through the eye or eyelids. Additional materials can be considered for the one or more support structure 112 as provided herein. The support structure 135 can include a coated plastic or metal material such that the coating contains a therapeutic agent. The support structure 135 can have a surface treatment such as plasma etching or the like to allow for suitable attachments to be made to the support structure 135, such as for example, the one or more body structures 112 as will be described in more detail below.

Again with respect to FIGS. 1A-1E and as mentioned above, the one or more body structures 112 can be tubular sections of material having an inner lumen 113 such that the support structure 135 can be threaded through the lumen 113 prior to fusing the ends of the support structure 135 together. In some implementations, the body structure 112 can be molded and cured into a particular shape, such as the tubular shape having a circular or other cross-section. FIG. 1C shows an implementation of a device 105 having two body structures 112a, 112b taken along circle C of FIG. 1B. A terminal end 111a of the first body structure 112a can abut a terminal end 111b of the second body structure 112b. FIG. 1D shows another implementation of a device 105 having two body structures 112a, 112b. In this implementation, the terminal ends 111a, 111b are separated a distance from one another other such that a region of the support structure 135 remains exposed. It should be appreciated that a single body structure 112 or more than two body structures 112 can be incorporated in the ocular device 105.

The ocular devices 105 can have any of a variety of cross-sectional shapes. In some implementations, the device 105 and/or the one or more body structures 112 can be circular in cross-section such the implementation shown in FIG. 1E. The device 105 and/or the one or more body structure 112 can also have a cross-section that is non-circular. For example a portion of the one or more body structures 112 in contact with the eye (such as the anterior surface of the eye) can be somewhat flattened. FIG. 1F illustrates a variety of other cross-sectional shapes including circular, lentoid, figure-eight, horseshoe, oval, oblong, rounded rectangle, star- or gear-shaped, etc. Generally, the edges of the ocular device in cross-section can be generally rounded. It should be appreciated that the cross-sectional shape can vary along different locations of the ocular device 105. In some implementations, the device 105 can have a cross-sectional thickness of between about 0.5 mm to about 1 mm. Further, the cross-sectional shape can be selected to maximize or otherwise increase the amount of surface area of the ocular device 105 as will be discussed in more detail below. In some implementations, the support structure 135 can have a cross-sectional diameter of between about 0.05 mm to about 0.35 mm, such that the inner diameter of each body structure 112 can be between about 0.06 mm to about 0.36 mm to accommodate the support structure therethrough. In some implementations, the support structure 135 can be between about 0.05 mm, 0.07 mm, 0.1 mm, 0.15 mm, 0.2 mm, 0.3 mm, or 0.35 mm in diameter. In some implementations, the support structure 135 can be a monofilament suture material having a size of between about USP 0, 2-0, 3-0, 4-0, 5-0, or 6-0 size suture material. The overall cross-sectional diameter of some implementations of the device can be approximately 0.5 mm to approximately 1.5 mm.

As mentioned above, the ocular device 105 can be configured to conform or mold in situ after positioning on the eye surface to the particular anatomical shape of the eye or shape of anatomy surrounding the eye. This allows for on-the-fly tailoring of the device shape providing the ocular device 105 with a comfortable fit that minimizes or eliminates irritation to the eye or anatomy surrounding the eye with minimal pre-existing information of a particular patient's eye shape. The ocular device 105 can have an initial, pre-insertion configuration or shape prior to being positioned in the eye. The material properties of the support structure 135, alone or in combination with the material properties of the one or more body structures 112, can determine the pre-insertion shape of the ocular device 105. The ocular device 105 can reconfigure from the initial, pre-insertion shape to a second, post-insertion configuration or shape. The pre-insertion shape can have an overall shape that is a flat or substantially flat ring or toroid shape. After application to the eye surface, the pre-insertion shape can begin to change towards the second, post-insertion shape, such as via plastic deformation or thermal activation of one or more components of the ocular device 105. The post-insertion shape can include an overall shape that generally conforms or molds to the patient's anterior surface of the eye as well as one or more components of the surrounding eye anatomy, including at least a portion of the conjunctiva of the eye and at least a portion of the bony orbit. As such, the pre-insertion configuration has a shape that is different from the shape of the post-insertion configuration. The device 105 can maintain the second post-insertion configuration even after the device 105 is removed from the eye. Alternatively, the device 105 can have a third post-removal configuration that has a shape different from one or both of the pre-insertion configuration shape and the post-insertion configuration shape.

Upon being removed from the eye, the device 105 can resist deflection away from the post-insertion and/or post-removal configuration shape. The pre-insertion shape can be an annular shape positioned substantially within a plane and the post-insertion and/or post-removal shapes can be positioned at least partially outside of that plane. In some implementations, the support structure 135 can have a self-loading resistance to deflection that is within a range from about 0.01 N/mm to about 1 N/mm. In additional implementations, the support structure 135 can have a first self-loading resistance to deflection between about 1 degree and about 60 degrees. The self-loading resistance to deflection of the support structure 135 can include a deflection angle between a first portion of the support structure 135 and a second portion of the support structure 135 when the first portion is supported and held in place and the weight of the second portion deflects the support structure 135. The one or more body structures 112 can be formed to have a self-loading resistance to deflection as well. The self-loading resistance to deflection of the one or more body structures 112 can be less than the self-loading resistance to deflection of the support structure 135.

The devices described herein can undergo an overall shape change upon being positioned on the eye, such as from a flat or substantially flat ring to the saddle shapes described herein. The device can also undergo a more localized shape changes. For example, one or more components of the devices described herein can undergo shape alteration such that the cross-sectional shape can change after implantation and due to contact made with certain eye anatomy. For example, the one or more body structures 112 can be formed of a generally soft, moldable material molded to have a circular cross-section. Over a period of time after being in contact with an eye structure, for example the fornix of the eye, the cross-section of the body structure 112 can mold to more closely mirror or conform to the surface shape of the eye structure with which the material is in contact. For example, a first portion of the outer surface of the body structure 112, such as the surface of the body structure 112 facing toward the anterior surface of the eye or the bulbar conjunctiva 344, can undergo a localized shape change after a period of time being in contact with that eye anatomy. Similarly, a second portion of the outer surface of the body structure 112, such as the surface of the body structure 112 facing towards the palpebral conjunctiva 342 of the eyelid, can also undergo a localized shape change after a period of time being in contact with that eye anatomy. In some implementations, the localized shape change of the outer surface portions can be from a convex spherical shape to a concave spherical shape. The cross-sectional shape of the one or more body structures 112 can change from a circular shape to a lentoid shape. In another implementation, the cross-sectional shape of the one or more body structures 112 can change from a circular shape to a figure eight shape. In another implementation, the cross-sectional shape of the one or more body structures 112 can change from a circular to a horse-shoe shape. It should be appreciated that the outer surface of the body structure 112 can take on or conform to any of a variety of local shapes depending upon the shape of the eye structures with which the outer surface of the body structure 112 makes contact. Thus, the devices described herein can undergo an overall shape change in situ determined primarily by the material properties of the support structure 135. The devices described herein can also undergo localized shape change in situ determined primarily by the material properties of the one or more body structures 112. Shape conformation of the devices described herein to the eye anatomy on both the large scale and the local scale, contribute to the comfort and retention of the device within the eye experienced by the patient.

As mentioned above, the ocular devices described herein can incorporate or couple to one or more therapeutic agents so as to release a safe and therapeutically effective quantity of the drug(s) into the eye upon implantation for a period of time. In some implementations, drug diffuses out of a silicone-drug matrix in a sustained release manner via drug elution. Release of a drug from the device can occur under any of a variety of ways and should not be limited to a particular chemical mechanism or formulation for the release and administration of drug to the eye. For example, the ocular devices described herein can release drug into the eye by drug elution, drug diffusion, biodegradation, controlled release, sustained release, and the like. In this regard, the ocular device 105 can be shaped to achieve a greater or lesser amount of surface area so as to achieve a desired drug release profile. For example, an increase in surface area of the one or more body structures 112 can achieve a higher level of drug release for the ocular device 105. In this regard, the surface area at one or more specific locations of the ocular device 105 can be selected to increase, decrease, or otherwise tune the rate of drug release from the specific area(s) of the ocular device 105 relative to other areas of the ocular device 105. This permits the ocular device 105 to have a rate of release at one location of the ocular device 105 that differs from the rate of release at another location of the ocular device 105.

The devices described herein can be formulated to achieve different drug release goals. For example, the devices described herein can incorporate a drug (such as for example within a body structure 112) to be released at a particular release rate to achieve a first drug dose in the eye. The devices described herein can also include a first drug at a first formulation, such as for example in a first body structure 112, and the first drug at a second formulation, such as for example in a second body structure 112. For example, the first formulation of the drug can allow for a higher drug dose released for a first period of time and the second formulation of the drug can allow for a lower drug dose released for a second longer period of time. Further, the devices described herein can include a first drug at a first formulation and a second drug at a second formulation allowing for a single device to deliver two (or more than two drugs) simultaneously. For example, the device 105 can include a first body structure 112 incorporating the first drug and a second body structure 112 incorporating the second drug and a third body structure 112 incorporating a third drug, etc. It should also be appreciated that the devices described herein can be formulated such that a single body structure 112 (or other component of the device) delivers more than a single drug. Further, it should be appreciated that components of the device other than the one or more body structures 112 can incorporate a drug. For example, the support structure 135 can be configured to incorporate a drug for release into the eye. There are a variety of ways in which the devices described herein can be designed to achieve a drug delivery release profile of interest. The one or more body structures 112, in particular, allow for a tailoring of treatment according to any of a variety of combination of doses, release rates, and therapeutics of interest.

The therapeutic agent can be placed on, embedded, encapsulated or otherwise incorporated into a delivery matrix. The delivery matrix can be included in or on either the support structure 135 or the one or more body structures 112, or both. The delivery matrix, in turn, can include either a biodegradable or a non-biodegradable material. The delivery matrix can include, although it is not limited to, a polymer. Examples of biodegradable polymers include protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid), and combinations thereof. Non-biodegradable polymers can include silicone, NuSil Med 4810, MED-4830 silicone, a silicone material, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CON-ICHROME® from Carpenter Metals Corp., Wyomissing, Pa.). In some implementations, the delivery matrix is a sustained drug delivery matrix material from Ocular Therapeutix (Bedford, Mass.), which incorporates a hydrogel technology that breaks down over time releasing the drug dispersed therein. In an implementation, the one or more body structures 112 can be formed of a delivery matrix, such as silicone, into which the one or more therapeutic agents can be dispersed or mixed into the matrix prior to molding and curing. In an implementation, the molded silicone can have a durometer in the range of about 10 Shore A to about 80 Shore A. In some implementations, the durometer is between 30 Shore A silicone and 50 Shore A silicone.

It should be appreciated that the implementations of the ocular devices described and shown in the figures are examples. The ocular devices can vary in shape, materials, and configurations from what is shown. For example, the ocular devices described herein need not be annular, but can rather form a portion of a ring. For example, the ocular devices can be substantially U-shaped or C-shaped. It should also be appreciated that the ocular devices described herein can include two or more separate structures that collectively form the ocular device 105. However, the ocular devices described herein can also be monolithic structures that are manufactured of a single material or a combination of materials while still providing the functional drug delivery and shape conformation capabilities.

Figure 2B:
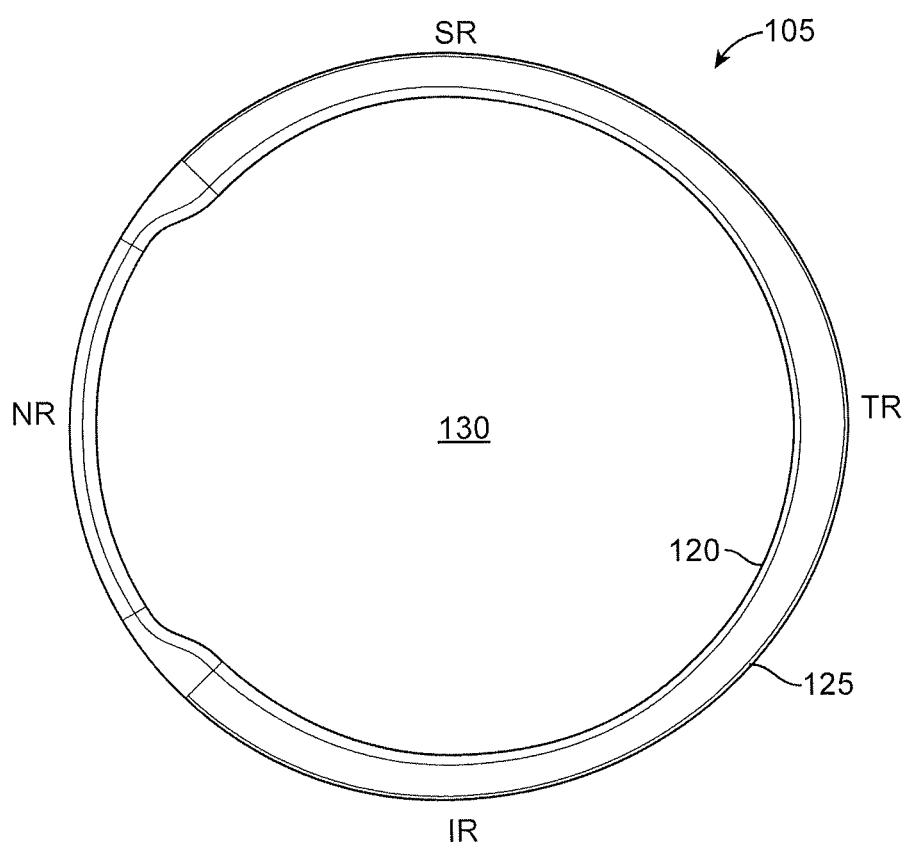
FIG. 2B shows a front view of the ocular device of FIG. 2A.

Now with respect to FIGS. 2A and 2B which show another implementation of an ocular device 105. As with the previous implementation, the ocular device 105 can have an annular configuration, such as an oval, circle or toroid shape, with an opening 130 that can be sized and shaped to fit outside the corneal diameter when positioned on the eye. Although the opening 130 can be sized to minimize contact and/or interference with the cornea when the ocular device is positioned on the eye, it should be appreciated that the ocular device 105 can occasionally contact the cornea such as when the patient is looking sideways. The device 105 can include a support structure 135 (represented by dashed line) coupled to a body structure positioned along a portion of or along the entire support structure 135. The ocular device 105 can include an outer surface 110, as well as an inner surface 115 that directly contacts the eye's anterior outer surface when the ocular device 105 is positioned on the eye. In addition, the ocular device 105 can include an anterior edge 120 that borders or surrounds the opening 130 of the ocular device 105. A posterior edge 125 can define an outermost contour of the ocular device 105. The posterior edge 125 and anterior edge 120 can each define a similar shape, for example a circular shape. Alternatively, the posterior edge 125 and the anterior edge 120 can have different shapes, for example the anterior edge 120 can be circular and the posterior edge 125 can be oval or some other shape. The opening 130 of the ocular device 105 can be centered or can be offset from center of the device 105. Generally, however, the opening 130 provides for the anterior edge 120 of the device to remain outside the optical zone of the eye.

Still with respect with FIGS. 2A and 2B, the ocular device 105 can generally include four regions, including a nasal region NR, a temporal region TR, a superior region SR, and an inferior region IR. The nasal region NR is generally configured to be positioned on a nasal region of the eye and the temporal region TR is configured to be positioned on a temporal region of the eye. Likewise, the superior region SR is configured to be positioned on a superior region of the eye while the inferior region IR is configured to be positioned on the inferior region of the eye. The regions NR, SR, TR, and IR of the ocular device can be particularly sized and shaped to interact with the corresponding regions of the eye so as to achieve fixation on the eye with minimal or no irritation to the eye. In this regard, the posterior edge 125, which defines the outer contour of the ocular device 105, can be sized and shaped such that each of the regions extends a desired distance in a posterior direction along the outer surface of the eye, as described more fully below. In addition, the regions of the ocular device can vary in geometry, size, thickness, width, etc. relative to one another. Any one of the regions can include an indent or other surface irregularity.

As mentioned above, the shape of the devices described herein can vary. In some implementations, the shape of the ocular device 105 can vary based on whether the ocular device 105 is to be positioned on the right eye or the left eye. The regions NR, SR, TR, and IR are not necessarily similarly shaped relative to one another. Rather, the regions can have differing shapes and can include one or more projections that are configured to increase the likelihood of the ocular device 105 being naturally retained on the eye for an extended period of time.

In the implementation of FIGS. 2A and 2B, the nasal region NR of the anterior edge 120 is shaped such that the distance between the anterior edge 120 and the posterior edge 125 is generally reduced relative to the remainder of the ocular device 105. In other words, the ocular device 105 has a reduced surface area in the nasal region NR for the implementation of FIGS. 2A and 2B. In addition, the temporal region of the ocular device 105 can extend further in a posterior direction than the remainder of the ocular device.

Figure 3:
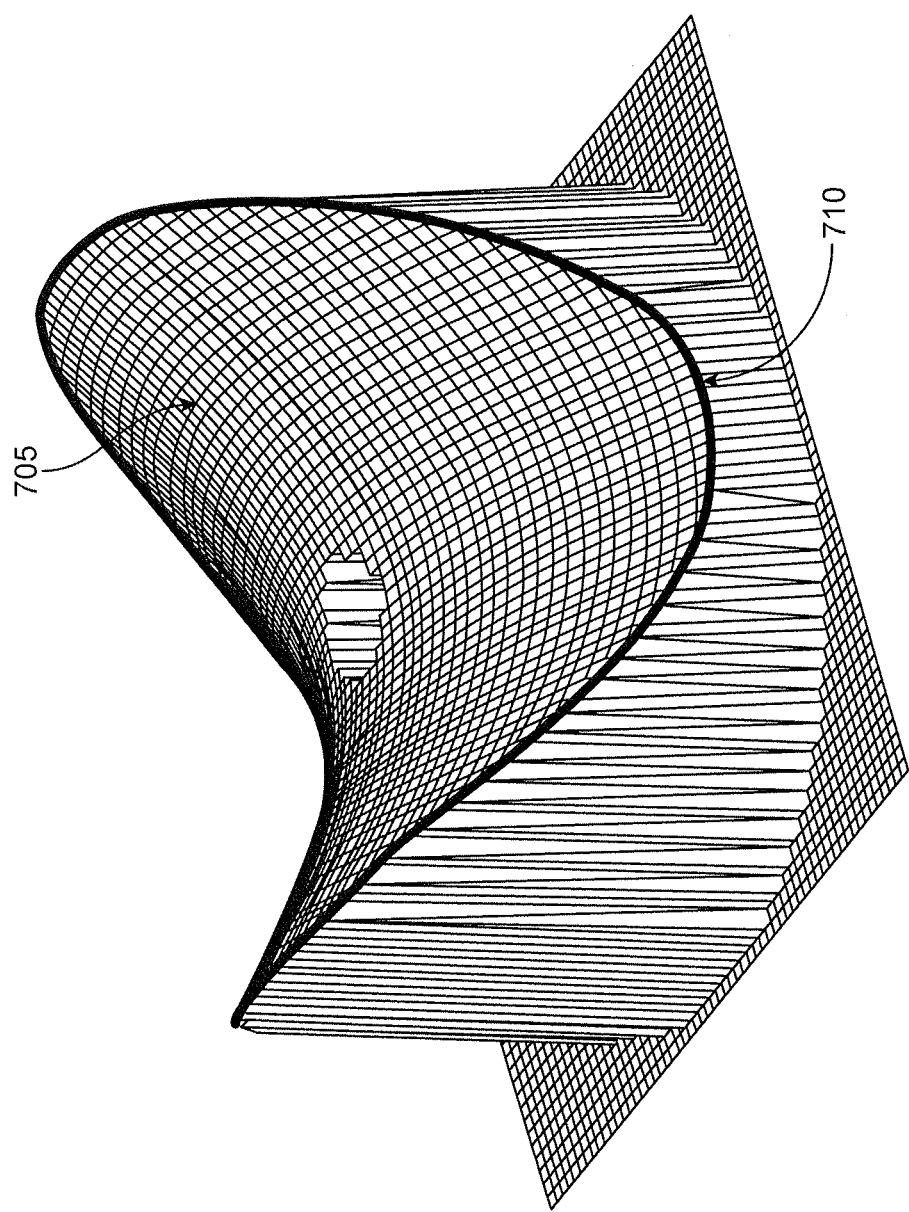
FIG. 3 shows a hyperbolic paraboloid surface.

The posterior edge 125 can have a shape that is configured to retain the ocular device 105 in a relatively fixed position once placed on the eye so as to reduce the likelihood of rotation or any other movement of the ocular device 105 relative to the eye. In an implementation, the posterior edge is defined by the surface of a regular or irregular saddle or hyperbolic paraboloid. FIG. 3 shows a hyperbolic paraboloid surface 705. A contour 710 is defined by the surface 705 and that contour 710 can correspond to the contour of the posterior edge 125 of an implementation of the ocular device, such as the implementation of FIGS. 2A and 2B. The surface 705 and/or the contour 710 can or cannot be symmetric around an x- and y-axis. For example, the shape and/or contour can vary based on whether the ocular device is positioned on the left eye or right eye. It should be appreciated that any of the implementations of the ocular device 105 described herein can have a contour that conforms to or substantially conforms to the contour 710 shown in FIG. 3.

As described above with respect to the device shown in FIGS. 1A-1E, any of the implementations of the ocular device 105 can be deformable, conformable, and/or moldable such that the overall shape of the device 105 changes in situ to the shape of the outer surface of the eye or surrounding anatomy when placed on the eye. With reference still to FIG. 3, the ocular devices 105 can have sufficient stiffness such that the posterior edge 125 conforms to a hyperbolic paraboloid surface even when the ocular device 105 is not positioned on the eye, such as prior to being positioned on the eye or after removal from the eye. Thus, in a stand-alone state, the posterior edge 125 of the ocular device 105 can conform to the surface of a hyperbolic paraboloid. In another implementation, the ocular device does not conform to such a shape prior to being positioned on the eye. In such an implementation, the ocular device can be flat or substantially flat prior to being positioned on the eye. The ocular device can then plastically deform or be activated to deform to a different shape after being positioned on the eye for a period of time. It should be appreciated that any of the devices described herein can reconfigure in situ from an initial, pre-insertion configuration to a second, post-insertion configuration. Further, that post-insertion configuration can be maintained even after the device is removed from the eye. Alternatively, the device can undergo a further shape change upon removal from the eye such that it takes on a post-removal configuration that can be the same or different from either the pre-insertion configuration or the post-insertion configuration.

Figure 4:
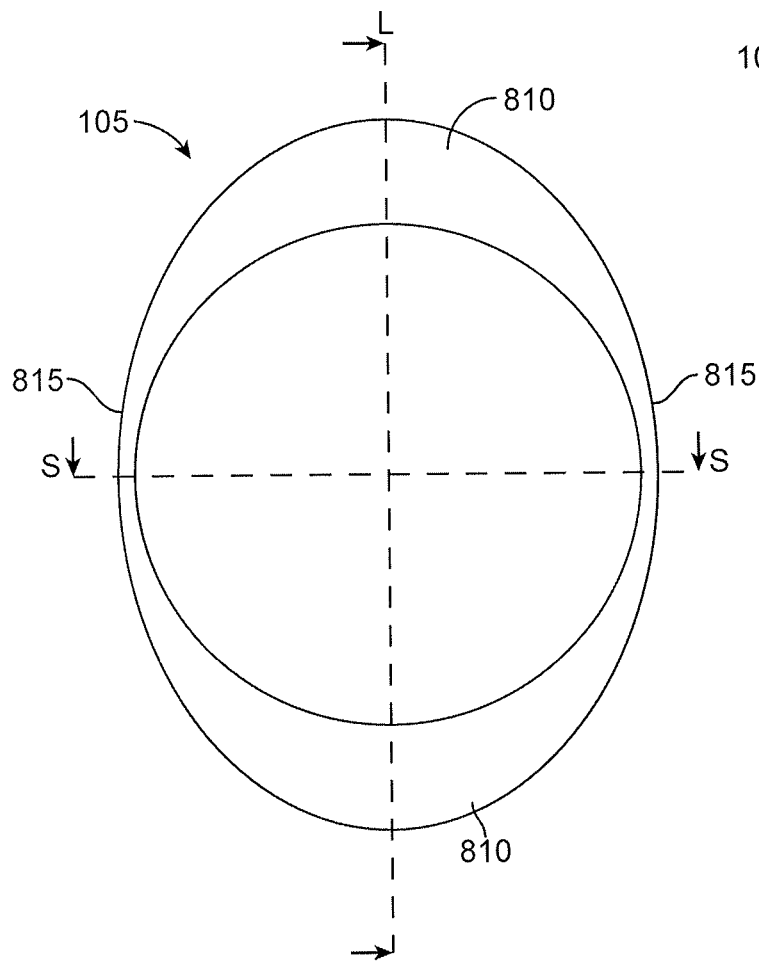
FIG. 4 shows a front view of an additional implementation of an ocular device.
Figure 5:
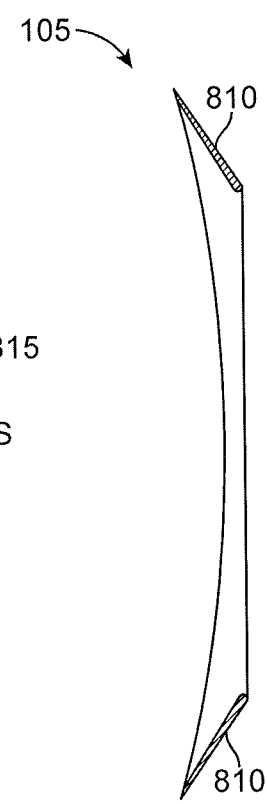
FIG. 5 shows a side view of the ocular device of FIG. 4.
Figure 6:
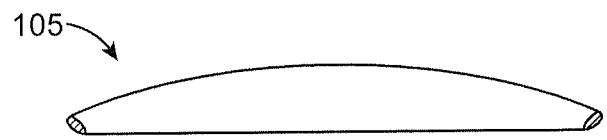
FIG. 6 shows a side view of the ocular device of FIG. 4.

FIGS. 4, 5 and 6 show another implementation of the ocular device 105. FIG. 4 shows a front view of the ocular device 105 while FIGS. 5 and 6 show side views. The ocular device 105 can have a generally round shape when viewed from the front, such as the shape of an oval. The shape can be defined by a long axis L and a short axis S. As mentioned, the shape can vary and it does not have to correspond to an oval or be round. Moreover, the ocular device can be symmetric or asymmetric about either of the long or short axes.

As shown in the side views of FIGS. 5 and 6, the ocular device 105 has a shape such that it is configured to be positioned on the spherical or substantially spherical outer surface of the eye. With reference to FIG. 4, the ocular device 105 can have a pair of enlarged or widened regions that form flaps 810 of increased surface area that are generally positioned along the long axis L of the ocular device 105 although their positions can vary. The flaps 810 can define a greater surface area than narrow regions 815, which are generally located along the short axis S of the ocular device 105. In the implementation of FIGS. 4-6, the flaps 810 can gradually taper or reduce in size moving from the location of the long axis L toward the location of the short axis S. It should be appreciated that the transition in size moving from the flaps 810 to the relatively smaller regions 815 can be less gradual or can be sudden. Moreover, the particular shape of the flaps 810, as well as the angle of the flaps with respect to an axis normal to the plane of FIG. 4, can vary to adjust surface area of the flaps, fit with the eye, retention, etc.

Figure 7:
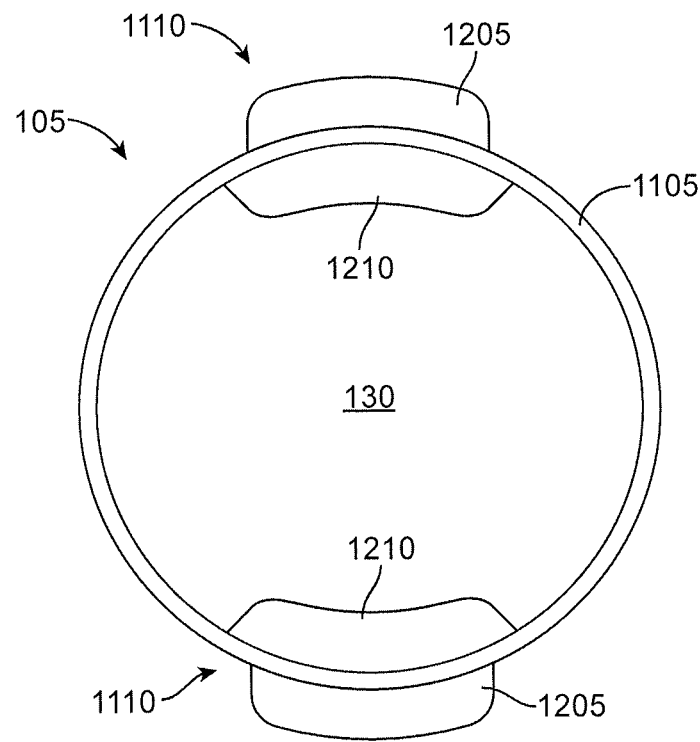
FIG. 7 shows a front view of another implementation of an ocular device.

FIG. 7 shows another implementation of an ocular device 105. When viewed from the front, the ocular device 105 can include a generally round body 1105 that forms a circle, ellipse, or other annular shape. At least one enlarged region, such as a flap 1110, can be positioned on the body 1105. The flap 1110 can have any of a variety of shapes. In general, the flap 1110 can be enlarged in thickness or width relative to a local region of the body 1105 where the flap 1110 is located.

In an implementation, each of the flaps 1110 positioned a circumferential distance away from the other flap 1110, such as about 180 degrees although the relative positions of the flaps can vary. Additionally, the number of flaps 1110 can vary including 1, 2, 3, 4, or more flaps 1110. The flaps 1110 each optionally include an outward region 1205 that extends outward relative to the body 1105. Each flap also optionally includes an inward region 1210 that extends inward toward the opening 130 of the body 1105. The flaps 1110 are sized and shaped to be positioned on the outer, spherical surface of the eye. The size and shape, and relative positions of the flaps 1110 can be selected to achieve a desired profile of fit, surface area, retention, etc. As mentioned, the implementation of FIG. 7 can vary in shape. For example, the body 1105 can be irregular in shape and can conform to the contour 710 of FIG. 3. The ocular device 105 can also include just the body 1105 without the flaps 1110.

Figure 8:
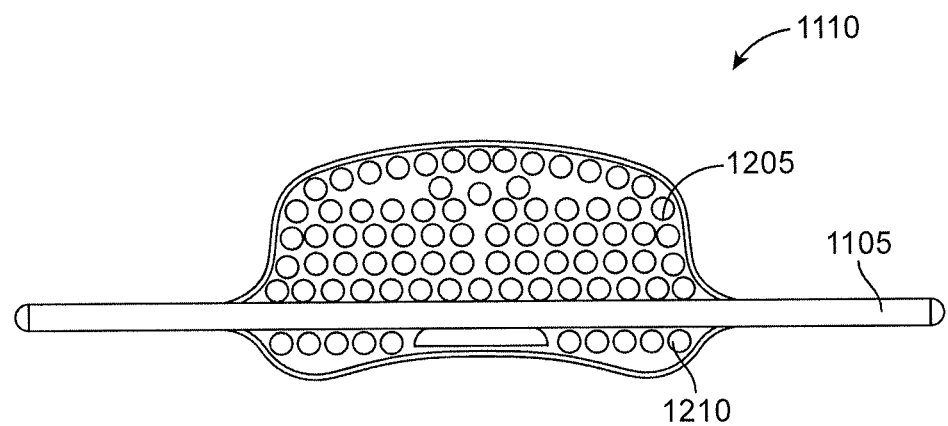
FIG. 8 shows an enlarged, front view of a portion of the ocular device in FIG. 7.

FIG. 8 shows an enlarged, front view of an implementation of one of the flaps 1110. As discussed, the flaps 1110 can include an outward region 1205 and an inward region 1210. In the illustrated implementation, the regions 1205 and 1210 are substantially rectangular in shape with rounded corners although it should be appreciated that the shape can vary. The surface of flap 1110 can includes one or more protrusions that are configured to increase the surface area of the flap 1110. Or, the flap 1110 can have a flat outer surface. Further, inward region 1210 of the flaps 1110 can have a surface geometry that conforms to a surface of a sphere as shown in FIG. 8.

FIG. 9 shows a perspective view of yet another implementation of an ocular device 105, which has a generally ring-like body 1305. FIGS. 10 and 11 show side views of the ocular device 105 of FIG. 9. The body 1305 can be formed of a thin, round band having a generally cylindrical outer surface. The body 1305 can have a pair of flaps 1310 that can extend at an angle relative to the plane defined by the circle of the body 1305. As shown in FIGS. 10 and 11, the flaps 1310 can be at a 90-degree angle relative to the plane of the body 1305, although the angle of the flaps 1310 can vary. The flaps 1310 can be stepped or tapered in width relative to the width of the body 1305. For example, a central region of each flap 1310 can be wider than each of the sides bordering the central region of each flap 1310. The taper can be gradual or sudden so as to form one or more steps in the shape of the flaps 1310.

Any of the implementations of the devices described herein can also include one or more haptics radiating from the ring-shaped structure. The haptics can also include at least one or more therapeutic agents.

Materials and Therapeutic Agents

The ocular devices described herein can be manipulated relatively easily during insertion onto the eye as well as removal from the eye, while still allowing for the conformation and molding in situ upon implantation onto the eye for improved comfort and retention on the eye.

A variety of materials can effect the shape changes described herein. One or more components of the devices described herein can be formed of or incorporate a variety of materials, such as those described herein. As mentioned above, the support structure 135 can effect shape changes of the device. The support structure 135 can be formed of a material providing an overall shape to the ocular device prior to the device being positioned on the surface of the eye. The support structure 135 can determine the shape of the device when the device is outside the eye prior to implantation, the shape the device conforms to in situ, as well as the shape of the device after removal of the conformed device from the eye. It should be appreciated that the shape changes can occur over a variety of periods of time, for example, from minutes to a period of days or months. In some implementations, shape conformation from a first shape prior to implantation onto the eye to a second shape after implantation onto the eye occurs over a period of about 20 minutes to about 24 hours.

The support structure 135 can be formed of one or more of a variety of materials including metal wire, filament or series of filaments, monofilament, a hard plastic such as nylon, PMMA, polycarbonate, polyethylene terephthalate, and/or another polymer, polypropylene or other synthetic suture material, or combinations of one or more of the above. Examples of materials that can stretch through spring action are also considered herein for one or more of the components of the device, including platinum alloys, titanium alloys, all stainless steel alloys & tempers, various clad metals and insulated wires. The ocular device can at least partially be made of a shape-memory material. In a non-limiting example, Nitinol can be used, which will allows the ocular device to change to a desired shape using thermal, magnetic or electromagnetic activation, from a martensitic to an austenitic state. Other examples of shape memory materials can be used, including, for example, shape memory polyurethanes, cross-linked trans-polyoctylene rubber, polynorbornene polymers, nitinol, polyethylene, PMMA, polyurethane, cross-linked polyethylene, cross-linked polyisoprene, polycycloocetene, polycaprolactone, copolymers of (oligo)caprolactone, PLLA, PL/DLA copolymers, PLLA PGA copolymers, thermoplastic polymers such as PEEK, cross-linked polyethylene terephthalate (PET) and polyethyleneoxide (PEO) block copolymers, block copolymers containing polystyrene and poly(1,4-butadiene), and other shape memory materials well-known to those of ordinary skill in the art. The material can also be any of material configured to repeatedly become plastic upon exposure to heat, liquid and/or pressure and harden upon cooling, drying, and/or removal of pressure.

In an implementation, one or more of the ocular devices described herein can expand as it absorbs fluid from the tear fluid in the eye or can stretch through a spring action mechanism. Examples of materials that can swell upon insertion in the eye include PVPE, PVA, polyurethane gels, and other types of hydrogels. One or more of the components of the devices described herein, such as support structure and/or body structure, can also be formed of one or more of a variety of materials including a biodegradable or a non-biodegradable material, such as silicone. The therapeutic agent can be placed on, embedded, encapsulated or otherwise incorporated into a delivery matrix. The delivery matrix, in turn, can include either a biodegradable or a non-biodegradable material. The delivery matrix can include, although it is not limited to, a polymer. Examples of biodegradable polymers include protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid), and combinations thereof. Non-biodegradable polymers can include silicone, MED-4830 silicone, a silicone material, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.). In some implementations, the delivery matrix is a sustained drug delivery matrix material from Ocular Therapeutix (Bedford, Mass.), which incorporates a hydrogel technology that breaks down over time releasing the drug dispersed therein. The devices described herein can also include material that can alter the rate of drug release into the eye from the device, including an elution rate altering material.

To prevent a potential allergic reaction to the ocular device in a patient, the ocular device, can include a hypoallergenic material. One or more of the components of the devices described herein, such as support structure and/or body structure, can include materials such as hydrogels, polyethylene glycol (PEG), or polyethylene oxide (PEO) that prevent adhesion of proteins and thus minimize the chance of developing an allergic reaction. Alternatively, the drug delivery matrix of the ocular device can include an anti-allergenic and/or antihistaminic compound to prevent an allergic reaction to the ocular device. In certain implementations, the delivery matrix can also include other materials known in the art. The ocular device can also be configured to reduce mucous.

It should be appreciated that these materials are provided as examples and are not intended to be limiting or all-inclusive of materials configured to provide the shape change capabilities of the devices and/or drug release capabilities of the devices described herein.

Table 1 shows examples of therapeutic agents suitable for use with the ocular devices described herein. The therapeutic agents can be used in many ways, and can include one or more of many therapeutic agents delivered.

TABLE 1

| Non-limiting Examples of Indications and Therapeutic Agents | |
|---|---|
| Indication | Therapeutic Agent |
| Glaucoma | Prostaglandin or prostaglandin analog or prostamide |

TABLE 1-continued

Non-limiting Examples of Indications and Therapeutic Agents

| Indication | Therapeutic Agent |
|---|---|
| Glaucoma | (e.g. Bimatoprost, Travoprost, Latanoprost, or Tafluprost etc.)<br>Prostaglandin or prostaglandin analog + second drug (e.g. latanoprost or bimatoprost)<br>Bimatoprost + Carbonic Anhydrase Inhibitor (CAI) (dorzolamide) |
| Glaucoma (Canine and/or other veterinary) | Prostaglandin or prostaglandin analog or prostamide (e.g. Bimatoprost, Travoprost, Latanoprost, or Tafluprost) |
| Corneal Transplant, Prevention of Rejection | Steroid |
| Bacterial Conjunctivitis | One or more newer antibiotics that have little resistance built up |
| Dry Eye | Cyclosporine<br>steroid (e.g. Loteprednol, Fluoromethalone)<br>Non-penetrating steroid (e.g. free acid of steroid)<br>Non-steroidal anti-inflammatories (e.g. Ketorolac)<br>Small-molecule integrin antagonist (e.g. Lifitegrast)<br>Doxycycline or azithromycin<br>Non-pharmacologic agent (e.g. lipid)<br>Fatty alcohol (e.g. cetyl alcohol or stearyl alcohol)<br>Fatty acid (e.g. long chain fatty acid)<br>Oil (e.g. silicone oil) |
| Post-Cataract Surgery | Antibiotic + Steroid;<br>(NSAID optional) |
| Post-Laser Surgery | Antibiotic + Steroid;<br>(NSAID optional) |
| Allergy | Olopatadine<br>Antihistamine<br>Steroid (e.g. Loteprednol, Fluoromethalone) |
| Trachoma | Doxycycline or other antibiotic |
| Blepharitis | Tetracycline, Doxycycline, Azithromycin, or other antibiotic<br>Non-pharmacologic agent (e.g. lipid)<br>Fatty alcohol (e.g. cetyl alcohol or stearyl alcohol)<br>Fatty acid (e.g. long chain fatty acid)<br>Oil (e.g. silicone oil) |

Alternatively or in combination with the therapeutic agents in Table 1, the therapeutic agent can include one or more of the following: an agent for lowering the intraocular pressure of the eye, anti-glaucoma medications, (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID), a decongestant (e.g., vasoconstrictor), an agent that prevents of modifies an allergic response (e.g., an antihistamine, cytokine inhibitor, leukotriene inhibitor, IgE inhibitor, immunomodulator), a mast cell stabilizer, cycloplegic or the like. Examples of conditions that can be treated with the therapeutic agent(s) include but are not limited to glaucoma, pre and post-surgical treatments, dry eye and allergies. In some implementations, the therapeutic agent can include a lubricant or a surfactant, for example a lubricant to treat dry eye.

The therapeutic agent can include a prostaglandin analog suitable for treatment of glaucoma as described herein. The prostaglandin analog can include one or more of latanoprost (XALATAN®), bimatoprost (LUMIGAN® or LATISSE®), carboprost, unoprostone, prostamide, travatan, travoprost, or tafluprost, for example. The therapeutic agent can also include a steroid, antibiotic, non-steroidal or "NSAID," loteprednol, cyclosporine, dexamethasone, dipivefrine, olopatadine, emedastine, antihistamine, moxifloxacin, natamycin, antifungal, polymyxin, neomycin, nepafenac, triamcinoline acetonide, tobramycin, prednisolone, rimexolone, fluorometholone, lodoxamide thromethamine, diflupredn ate, brinzolamide, metipranolol, timolol, aproclonidine, carbachol, pilocarpine, cyclopentate, atropine, betaxolol, brimonidine, nedocromil, epinastine, alcaftadine, ketorolac, lifitegrast, prednisolone, gatifloxacin, bepotastine, besifloxacin, bromfenac, fluocinolone, ganciclovir, tobramycin, hydroxypropyl cellulose, azithromycin, dorzolamide, levofloxacin, ofloxacin, bunazosin, unoprostone, levocabastine, sodium hyaluronate, diquafosol, fluorometholone, pirenoxine, or latanoprostene bunod.

The therapeutic agent can include one or more of the following or their equivalents, derivatives or analogs: thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; antisecretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Anti inflammatory steroids contemplated for use in the methodology of the implementations described here, include corticosteroids, for example, triamcinolone, dexamethasone, fluocinolone, cortisone, prednisolone, flumetholone, loteprednol, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil3; immunological drugs (such as vaccines and immune stimulants); hormonal agents (such as estrogens,—estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as bimatoprost, travoprost, Latanoprost, tafluprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

It should be appreciated that these therapeutic agents are provided as examples and are not intended to be limiting or all-inclusive of therapeutic agents that can be delivered using the devices described herein. Further it should be appreciated that a variety of drug loading and dosing of the various therapeutic agents are considered herein such as the drug loading and dosing described in U.S. Patent publication number 2012/0136322, entitled ANTERIOR SEGMENT DRUG DELIVERY, filed Jun. 1, 2011; and U.S. Patent publication number 2013/0144128, entitled OCULAR INSERT APPARATUS AND METHODS, filed Sep. 14, 2012, each of which are incorporated by reference herein.

The devices described herein can be manufactured according to a variety of methods. In one implementation, a drug can be mixed and dispersed into a drug matrix, such as a medical grade silicone like MED-4830 silicone to form a body structure 112 of drug-drug matrix material. The drug-drug matrix material of the body structure 112 can be molded and cured into a desired shape. For example, the material of the body structure 112 can be molded and cured as is known in the art. In some implementations, the body structure 112 can be molded into an elongate tubular structure having a lumen 113 extending therethrough. The tubular structure can have a variety of cross-sectional shaped as discussed herein including, but not limited to circular, lentoid, figure-eight, horseshoe, oval oblong, rounded rectangle, star- or gear-shaped, etc. In some implementations, at least a portion of the body structure 112 can have a cross-sectional thickness that is approximately 1 mm. The lumen 113 extending through each of the body structures 112 can have an inner diameter configured to receive the support structure 135. In some implementations, the lumen 113 can have an inner diameter of about 0.06 mm, 0.08 mm, 0.11 mm, 0.16 mm, 0.21 mm, 0.31 mm, or 0.36 mm in diameter. Each of the body structures 112 can vary in length, such as for example, at least about 1 mm, 2, mm, 4 mm, 6 mm, 8 mm, 10 mm, 12 mm, 14 mm, 16 mm, 18 mm, or greater up to the length of the support structure 135 onto which the body structure 112 is thread. The length of the body structures 112 can create an arc length of the support structure 135. For example, one body structure 112 can create an arc length of between about 5 degrees to 75 degrees to approximately 360 degrees, such that the support structure 135 is completely covered by the single body structure 112. The ocular device 105 can have an arc length of approximately 5 degrees to approximately 75 degrees to approximately 175 degrees each, as well as any length therebetween. It should also be appreciated that the body structure 112 can be thread onto the support structure 135 such that the body structure 112 is positioned onto the support structure 135 according to one of a variety of positions relative to the support structure 135 and relative to each other if more than a single body structure 112 is incorporated on the device 105.

One or more of the body structures 112 can be threaded over a support structure 135. The support structure 135 can be stress relieved in an oven and thermoformed into a ring shape or other shape, for example by wrapping the support structure 135 around a mandrel having a selected diameter. The shaped support structure 135 can be cut to a desired length, such as for example 24 mm, 25 mm, 26 mm, 27 mm, 28 mm, or 29 mm. The support structure 135 can be heat-set to a ring or other shape prior to or after trimming to a desired length. The one or more body structures 112 can be threaded over the support structure 135 prior to thermally welding the ends of the support structure 135 together. Once the one or more body structures 112 are threaded over the support structure 135, the free ends of the support structure 135 can be fused together such as by thermally welding them to form a full ring shape. Each device 105 can be placed into a packaging tray and terminally sterilized by e-beam irradiation.

Eye Anatomy and Methods of Use

The ocular devices described herein are generally sized and shaped to be positioned on an outer surface of the eye with at least a portion of the ocular device positioned under one or both eyelids in a manner that does not contact or interfere with the cornea. The anatomy of the eye will now described along with example methods of implantation and use.

Figure 12:
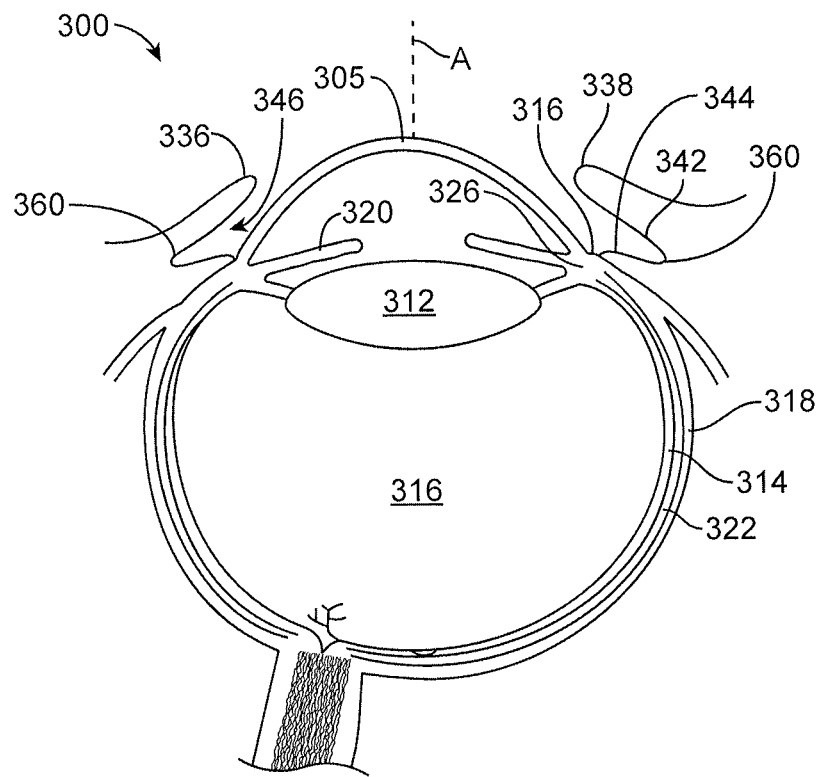
FIG. 12 shows a cross-sectional, schematic view of an eye suitable for incorporation with the ocular device.

FIG. 12 shows an eye 300 suitable for incorporation with the ocular devices described herein. The eye has a light transmitting cornea 305 and a light-transmitting lens 312 that forms an image on the light-sensing retina 314 so that the person can see. The eye 300 includes a light-transmitting vitreous humor 316 between the lens 312 and retina 314. A reference axis A can include one or more known axes of the eye such as the visual axis, the line of sight, the optical axis, or other axis of the eye. The cornea 305 extends to a limbus 316 of the eye, and the limbus 316 connects to a sclera 318 of the eye. The eye has an iris 320 that can expand and contract in response to light. The eye also includes a choroid 322 disposed between the sclera 318 and the retina 314. The eye further includes a pars plana 326 located along the scleral portion of the eye near the limbus 316.

With reference to FIGS. 12-15, the eye 300 includes connective tissue structures to protect the eye and allow the eye to move. Lids are configured to open to allow the eye to see and close to protect the eye. An upper lid 336 extends across an upper portion of the eye and a lower lid 338 extends across a lower portion of the eye. The eyelids define a palpebral fissure extending between the upper lid 336 and lower lid 338. The conjunctiva is a loose tissue that protects the eye and allows the eye to move within the bony socket. The conjunctiva includes a lid portion including a palpebral conjunctiva 342 and a globe portion including bulbar conjunctiva 344. The palpebral conjunctiva 342 lines the inner surface of the upper and lower eyelids that contact the cornea 305 when the eyelids close. The conjunctiva extends from the palpebral conjunctiva 342 of each lid to the bulbar conjunctiva 344 located over the sclera 318 of the eyeball. The bulbar conjunctiva 344 connects to the eyeball near the limbus 316. The conjunctiva extends from the palpebral conjunctiva 342 of each eyelid and reflects back to form a sac 346 including a cul-de-sac 510 and a fornix 360. The bulbar conjunctiva 344 is located over the sclera 318 and translucent such that the white sclera can be readily seen.

Figure 13:
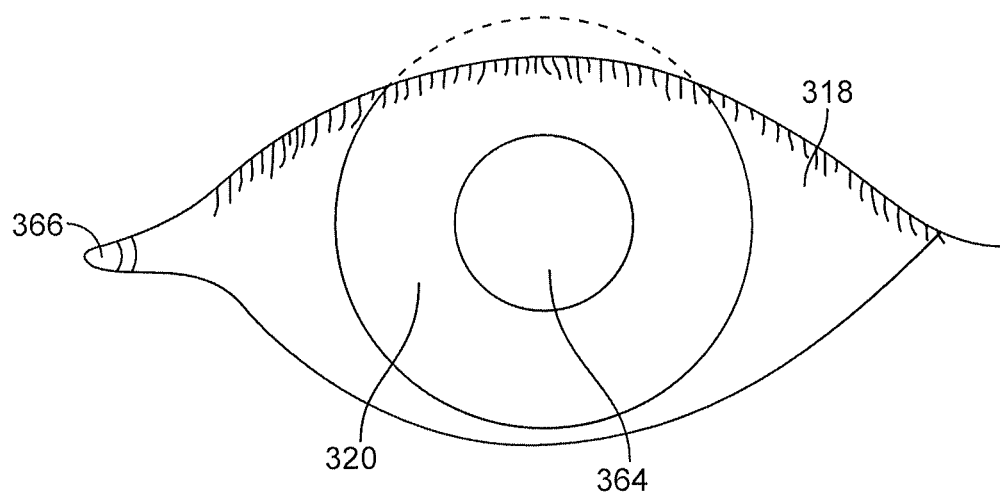
FIG. 13 shows a front view of the eye of FIG. 12.

FIG. 13 shows front view of the eye. The pupil 364, iris 320 and sclera 318 can be readily seen with a front view of the eye. The medial canthus is located on a nasal end of the palpebral fissure, and the lateral canthus is located on a lateral end of the palpebral fissure. The human eye further includes a caruncle 366, which is located nasally near the medial canthus. A fold of the bulbar conjunctiva 344 including the plicasemilunaris can be located near the caruncle 366. As the plicasemilunaris can move with the eyeball, the plicasemilunaris can move nasally under the caruncle when the patient looks nasal and can become increasingly visible when the patient looks temporally so as to rotate the plicasemilunaris temporally. The eye can include additional folds of the bulbar and palpebral conjunctiva that extend circumferentially around the eye so as to allow the eye to rotate freely within the bony orbit.

Figure 14:
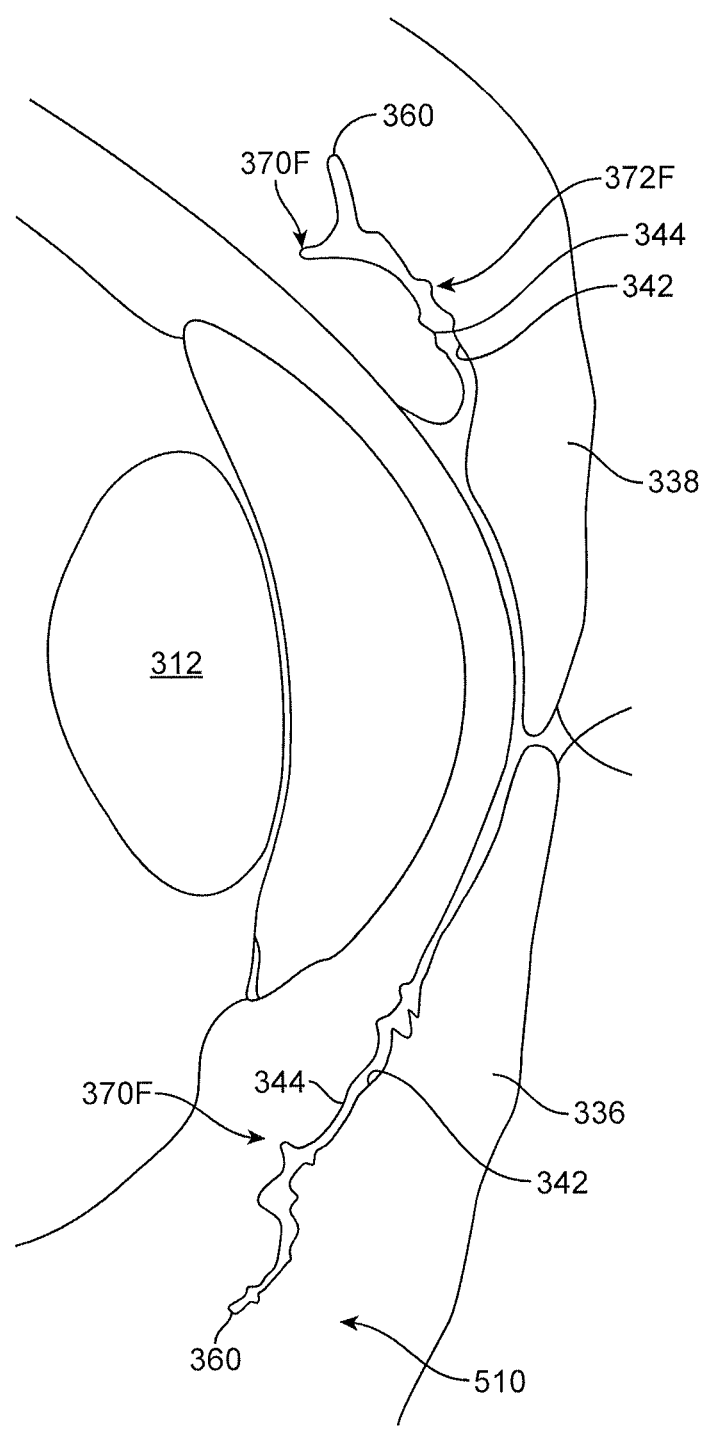
FIG. 14 shows a side, cross-sectional, schematic view of the eye including the conjunctiva of the upper lid and lower lid.

FIG. 14 shows a side, sectional view of the conjunctiva of the upper lid 338 and lower lid 336 of the eye. The bulbar portion 344 of the conjunctiva includes a plurality of folds 370F and the palpebral portion 342 of the conjunctiva includes a plurality of folds 372F. The conjunctiva reflects back between the bulbar conjunctiva 344 and the palpebral conjunctiva 342 at the fornix 360. The plurality of bulbar folds 370F and the plurality of palpebral folds 372F can each extend substantially circumferentially around at least a portion of the eye. The sac 346 includes the cul-de-sac 510, and the cul-de-sac 510 includes the fornix 360.

Figure 15:
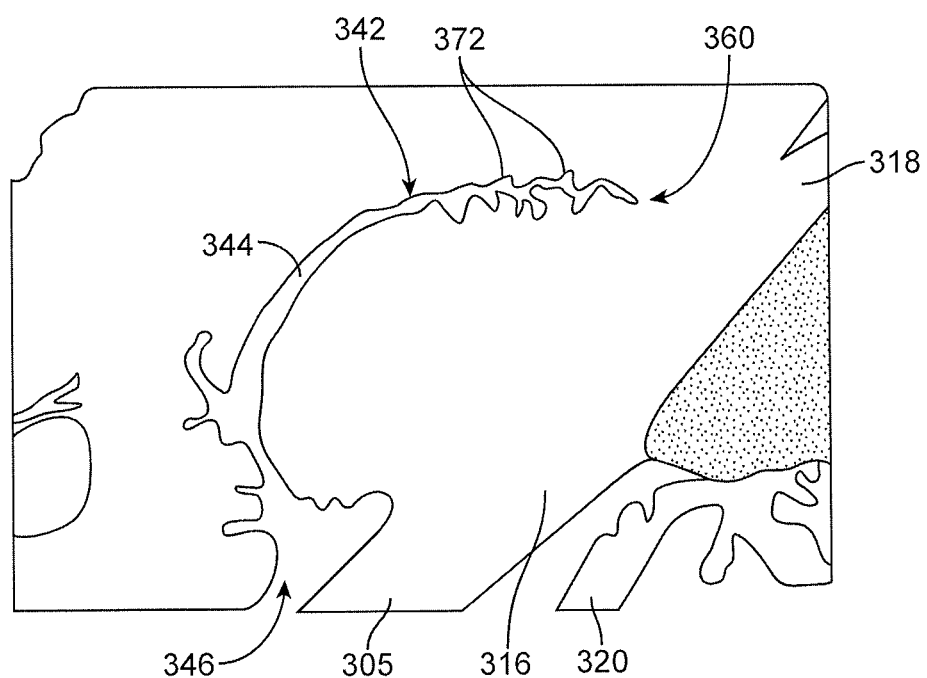
FIG. 15 shows a side, cross-sectional, schematic view of the upper lid and the folds of the conjunctiva of the eye.

FIG. 15 shows a side sectional view of the upper lid of the eye and the folds of the conjunctiva. The bulbar conjunctiva 344 of the upper lid 338 has many folds 370F along the conjunctiva extending between the limbus and the fornix 360. The palpebral conjunctiva 342 of the upper lid includes many folds 372F extending between the fornix and the lower margin of the upper eyelid 338. The bulbar conjunctiva 344 of the lower lid 336 has many folds 370F along the conjunctiva extending between the limbus and the fornix 360, and the palpebral conjunctiva 342 of the lower lid 336 includes many folds 372F extending between the fornix and the upper margin of the lower lid 336.

Figure 16:
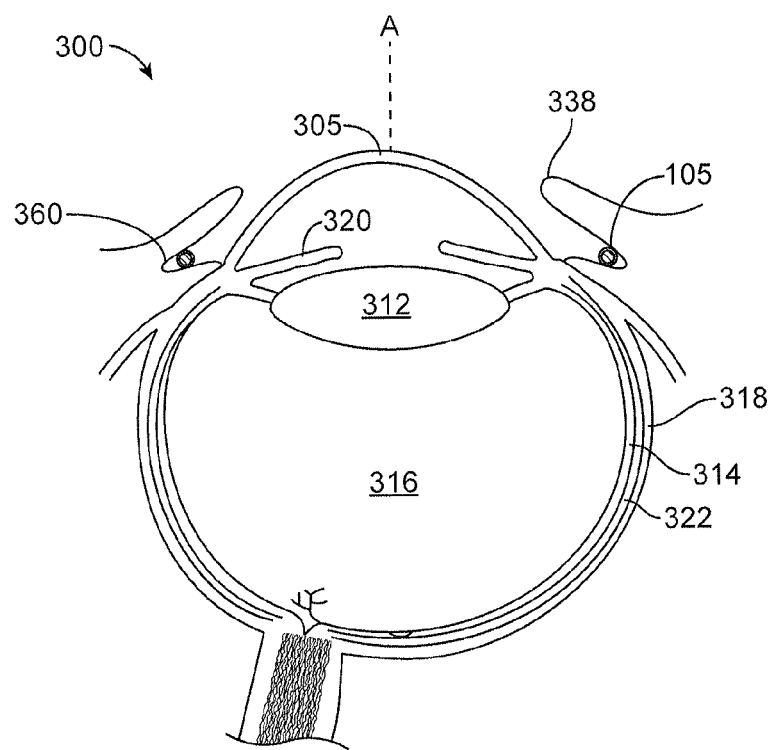
FIG. 16 shows an implementation of a device positioned on the eye.

FIG. 16 shows an implementation of an ocular device 105 inserted onto the anterior surface of the eye and positioned within the upper and lower fornices 360. The device 105 can be inserted onto the eye using a variety of techniques with or without anesthetic agent. In one implementation, the device 105 can be placed following administration of a topical anesthetic. The eyelids can be gently spread apart and using a blunt-ended instrument or fingers, the device can be placed in the upper and lower fornices. For example, the device 105 can be inserted first in the upper fornix such that the device is held within the upper fornix while the device is being placed in the lower fornix. It should be appreciated that the opposite procedure in which the device is first placed in the lower fornix prior to insertion into the upper fornix is to be considered herein. After insertion, the ocular device 105 can be retained in position on the eye for a period of time without the use of any mechanical fastening elements that extend into or through eye tissue. The device can be held naturally, for example, by its interaction with the normal anatomy of the eye supplemented by the shape conformation of the device that can occur over time. Once in position, the device is generally not visible during a normal gaze with the exception perhaps of a small segment of the device that may be visible in the nasal area of the eye near the caruncle. To remove the device from the eye, an optional drop of anesthetic agent can be applied to the eye prior to grasping the device in the lower fornix (usually using a blunt-ended instrument), and gently removing the device from the eye.

The device can be used to treat the eye over a period of time. The period of time for which the ocular device 105 can be positioned on the eye for effective treatment can vary including, but not limited to at least any of one of 1 day, 5 days, one week, one month, two months, three months, four months, six months or a greater amount of time.

Figure 17:
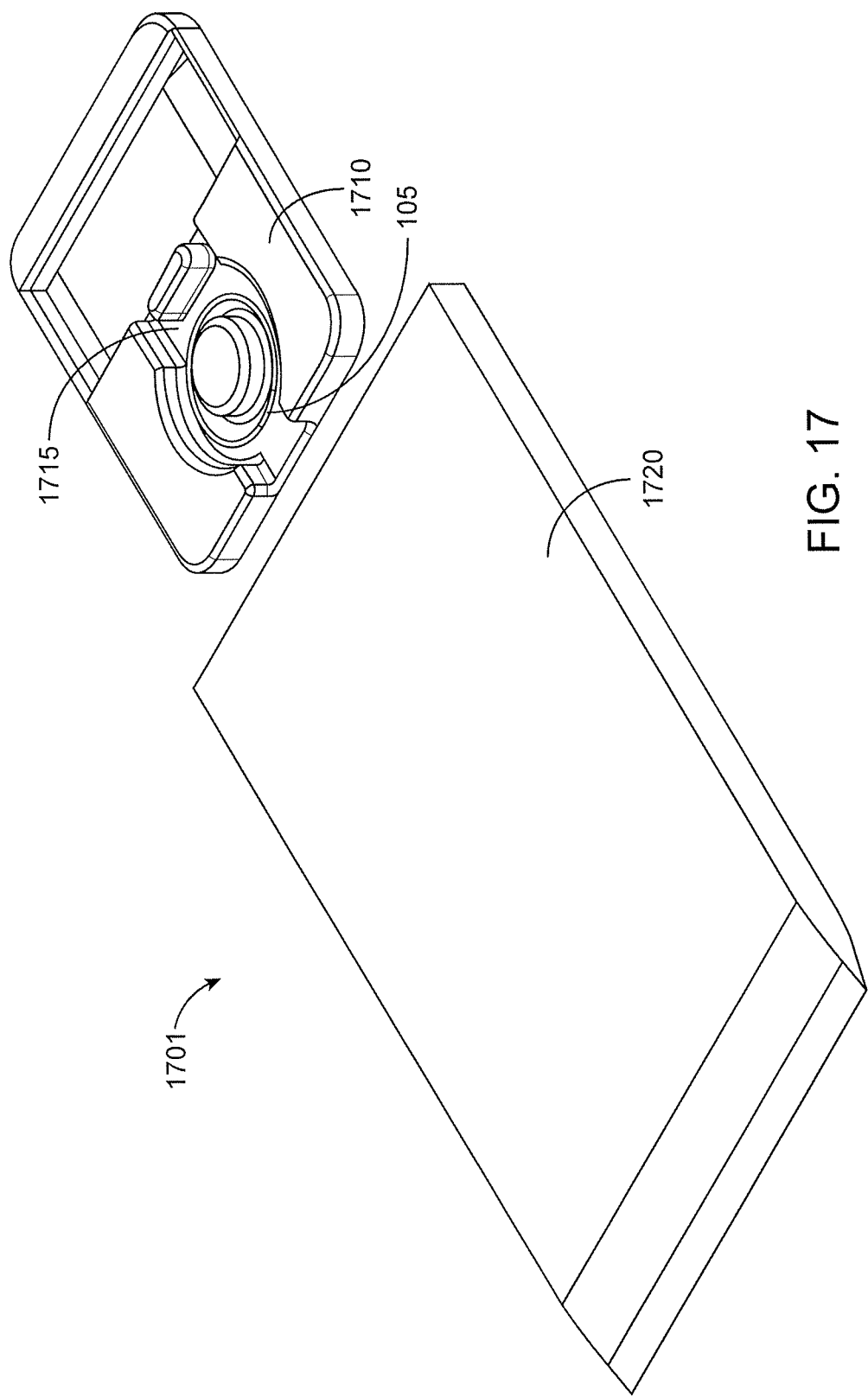
FIG. 17 shows an exploded view of an implementation of a device and packaging.

FIG. 17 shows an exploded view of an implementation of an ocular device 105 within packaging 1701. Each ocular device 105 can be placed in a packaging tray 1710 and terminally sterilized by e-beam irradiation. The packaging tray 1710 can include a complementary-shaped well 1715 configured to safely retain the ocular device 105 within the tray 1710, for example, upon breaking open a foil pouch 1720 upon use. The ocular device 105 can be disposed within the tray 1710 bathed in a non-therapeutic solution, for example, saline. One or more of the ocular devices 105 described herein can be provided in the form of a kit containing the packaging tray 1710 holding the ocular device 105. In some implementations, the kit can further include instrumentation configured to aid in the positioning of the device 105 in the eye, a small amount of anesthetic, and directions for use. In some implementations, the kit can include a plurality of ocular devices 105. For example, one kit can include multiple sizes of ocular devices for fitting different sized eyes. The ocular devices described herein can have an overall diameter of approximately 24 mm, 25 mm, 26 mm, 27 mm, 28 mm, or 29 mm to accommodate various eye sizes. It should be appreciated that the drug content of each device can be the same irrespective of size. Alternatively, one kit can include multiple ocular devices for the treatment of a single patient over a period of time such that as one device is used and removed, an additional device can be inserted.

While this specification contains many specifics, these should not be construed as limitations on the scope of an invention that is claimed or of what can be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations can be made based on what is disclosed.

What is claimed is:

1. An ocular device configured to be positioned on a surface of the eye at least partially underneath at least one of the upper and lower eyelids and outside a cornea of the eye for delivering at least one therapeutic agent to an eye for an extended period of time, the device comprising:
   a thin, elongated filamentous first structure formed of a first material;
   a second structure formed of a second material having a tubular structure such that the first structure extends through a lumen of the tubular structure, wherein the second material is different from the first material; and
   at least one therapeutic agent dispersed within at least one of the first material of the first structure or the second material of the second structure,
   wherein the second structure has at least two grooves formed in an outer surface of the tubular structure providing a cross-sectional shape to the tubular structure along a cross-section taken across the lumen from an anterior surface to a posterior surface of the tubular structure, wherein the outer surface is configured to contact a surface of the eye upon positioning the ocular device outside the cornea.

2. An ocular device as in claim 1, wherein the cross-sectional shape is selected from the group consisting of figure-eight or gear-shaped.

3. An ocular device as in claim 1, wherein the first structure is thermally fused into a ring shape after being threaded through the lumen of the second structure.

4. An ocular device as in claim 1, wherein the second structure formed of a second material is molded into two or more tubular structures, wherein each of the two or more tubular structures has a lumen through which the first structure extends.

5. An ocular device as in claim 4, wherein a first of the two or more tubular structures is formulated to release the at least one therapeutic agent and wherein a second of the two or more tubular structures is formulated to release the at least one therapeutic agent or at least a second therapeutic agent dispersed within the second material of the second structure, wherein the at least one therapeutic agent and the at least a second therapeutic agent are the same or different therapeutic agents.

6. An ocular device as in claim 1, wherein the first material is non-erodible and has a stiffness that conforms into a second, different shape after positioning the ocular device on the surface of the eye, and wherein upon being removed from the eye, the ocular device retains the second shape or changes to a third shape, wherein the third shape is different from both the first shape and the second shape.

7. An ocular device as in claim 6, wherein the second shape is a shape of at least a portion of the conjunctiva of the eye.

8. An ocular device as in claim 6, wherein the second shape is a shape of at least a portion of the bony orbit of the eye.

9. An ocular device as in claim 7, wherein the second shape is a shape of at least a portion of bony orbit of the eye.

10. An ocular device as in claim 6, wherein the ocular device resists deflection away from the second shape upon being removed from the eye.

11. An ocular device as in claim 6, wherein the first shape is an annular shape positioned substantially within a first plane and the second and third shapes are positioned at least partially outside of the first plane.

12. An ocular device as in claim 6, wherein the second shape corresponds to a surface of a saddle.

13. An ocular device as in claim 6, wherein the second shape has an outer contour that corresponds to an outer contour of a saddle.

14. An ocular device as in claim 6, wherein the ocular device changes from the first shape to the second shape over a period of about 20 minutes to about 24 hours.

15. An ocular device as in claim 1, wherein the first material comprises a material configured to repeatedly become plastic upon exposure to heat, liquid, or pressure.

16. An ocular device as in claim 1, wherein the first material comprises a thermoplastic material.

17. An ocular device as in claim 16, wherein the first material comprises polypropylene.

18. An ocular device as in claim 1, wherein the second material comprises a silicone material.

19. An ocular device as in claim 18, wherein only the second material comprises the at least one therapeutic agent.

20. An ocular device as in claim 1, wherein the at least one therapeutic agent comprises an agent selected from the group consisting of bimatoprost, travoprost, latanoprost, tafluprost, NSAID, steroid, antihistamine, carbonic anhydrase inhibitor (CAI), dorzolamide, cyclosporine, antibiotic, doxycycline, tetracycline, azithromycin, fatty acid, long chain fatty acid, fatty alcohol, cetyl alcohol, stearyl alcohol, non-penetrating steroid, free acid of steroid, lipid, ketorolac, silicone oil, olopatadine, prostaglandin, prostaglandin analog, prostamide, small-molecule integrin antagonist, lifitegrast, loteprednol, and fluoromethalone or a combination thereof.

21. An ocular device as in claim 1, wherein the at least one therapeutic agent comprises a prostaglandin analogue.

22. An ocular device as in claim 21, wherein the prostaglandin analogue comprises at least one of bimatoprost, latanoprost, travoprost, and tafluprost.

23. An ocular device as in claim 1, wherein the at least one therapeutic agent is for lowering the intraocular pressure of the eye.

24. An ocular device as in claim 1, wherein the at least one therapeutic agent is for treating dry eye.

25. An ocular device as in claim 24, wherein the at least one therapeutic agent comprises at least one of cyclosporine, steroid, loteprednol, fluoromethalone, non-penetrating steroid, free acid of steroid, non-steroidal anti-inflammatory, ketorolac, small-molecule integrin antagonist, lifitegrast, doxycycline, azithromycin, lipid, fatty alcohol, cetyl alcohol, stearyl alcohol, fatty acid, long chain fatty acid, oil, or silicone oil.

26. An ocular device as in claim 1, wherein the at least one therapeutic agent comprises a steroid.

27. An ocular device as in claim 26, wherein the steroid comprises at least one of loteprednol or fluoromethalone.

28. An ocular device as in claim 1, wherein the cross-sectional shape of the tubular structure increases a surface area of the second structure and an elution rate of the at least one therapeutic agent from the device.

29. An ocular device as in claim 1, wherein the tubular structure has a maximum cross-sectional diameter and a surface area exposed to the eye, wherein the maximum cross-sectional diameter is between 0.5 mm and 1.5 mm.

30. An ocular device as in claim 29, wherein the cross-sectional shape varies along a circumferential length of the device.

\* \* \* \* \*